(12) United States Patent
Heymann et al.

(10) Patent No.: US 9,403,873 B2
(45) Date of Patent: Aug. 2, 2016

(54) PEPTIDES TARGETING RECEPTOR ACTIVATOR OF NUCLEAR FACTOR-κB (RANK) AND THEIR APPLICATIONS

(71) Applicants: UNIVERSITE DE NANTES, Nantes (FR); CHU NANTES, Nantes (FR)

(72) Inventors: Dominique Heymann, Indre (FR); Stéphane Teletchea, Bouguenais (FR); Verena Stresing, Nantes (FR)

(73) Assignees: UNIVERSITE DE NANTES, Nantes (FR); Chu Nantes, Nantes (FR)

( * ) Notice: Subject to any disclaimer, the term of this patent is extended or adjusted under 35 U.S.C. 154(b) by 0 days.

(21) Appl. No.: 14/368,080

(22) PCT Filed: Dec. 21, 2012

(86) PCT No.: PCT/EP2012/076729
§ 371 (c)(1),
(2) Date: Jun. 23, 2014

(87) PCT Pub. No.: WO2013/093039
PCT Pub. Date: Jun. 27, 2013

(65) Prior Publication Data
US 2014/0371150 A1 Dec. 18, 2014

(30) Foreign Application Priority Data
Dec. 23, 2011 (EP) .................................. 11306766
Jul. 20, 2012 (EP) .................................. 12305886

(51) Int. Cl.
| | | |
|---|---|---|
| A61K 38/08 | (2006.01) | |
| A61K 38/10 | (2006.01) | |
| C07K 7/06 | (2006.01) | |
| C07K 7/08 | (2006.01) | |
| A61P 19/02 | (2006.01) | |
| A61P 19/08 | (2006.01) | |
| A61P 19/10 | (2006.01) | |
| A61K 38/04 | (2006.01) | |
| A61K 45/06 | (2006.01) | |
| A61K 47/48 | (2006.01) | |

(52) U.S. Cl.
CPC . *C07K 7/06* (2013.01); *A61K 38/04* (2013.01); *A61K 38/08* (2013.01); *A61K 38/10* (2013.01); *A61K 45/06* (2013.01); *A61K 47/48215* (2013.01); *C07K 7/08* (2013.01)

(58) Field of Classification Search
None
See application file for complete search history.

(56) References Cited

U.S. PATENT DOCUMENTS

2004/0031072 A1 2/2004 La Rosa et al.
2007/0044171 A1 2/2007 Kovalic et al.

OTHER PUBLICATIONS

Ta et al., Proc. Nat'l. Acad. Sci. USA, Nov. 2010, vol. 107(47):20281-20286.*
Poblenz et al., Biochem. Biophys. Res. Commun., 2007, vol. 359(3):510-515.*
Aoki et al., J. Clin. Invest., 2006, vol. 116(6):1525-1534.*
Heath et al., Cancer Res., 2007, vol. 67(1):202-208.*
International Search Report dated Mar. 19, 2013 (PCT/EP2012/076729); ISA/EP.
International Preliminary Examination Report dated Dec. 16, 2013 (PCT/EP2012/076729); IPEA/EP.
Ta Hai Minh et al: "Structure-based development of a receptor activator of nuclear factor-kappa B ligand (RANKL) inhibitor peptide and molecular basis for osteopetrosis", Proceedings of the National Academy of Sciences of the United States of America. vol. 107. No. 47. Nov. 2010, pp. 20281-20286, XP002676814, ISSN: 0027-8424, abstract, table 1.
Poblenz et al: "Inhibition of RANKL-mediated osteoclast differentiation by selective TRAF6 decoy peptides" Biochemical and Biophysical Research Communications. Academic Press Inc. Orlando, FL, US, vol. 359, No. 3, Jun. 15, 2007, pp. 510-515, XP022117678, ISSN: 0006-291X, DOI: 10.1016/J. BBRC.2007.05.151 abstract.
Kazuhiro Aoki et al: "A TNF receptor loop peptide mimic blocks RANK ligand-induced signaling, bone resorption, and bone loss", Journal of Clinical Investigation, American Society for Clinical Investigation, US, vol. 116, No. 6, Jan. 1, 2006, pp. 1525-1534, XP008126832, ISSN: 0021-9738, DOI: 10.1172/JCI22513 abstract, p. 1531, right-hand column, paragraph 3.
D. J. Heath et al: "An Osteoprotegerin-like Peptidomimetic Inhibits Osteoclastic Bone Resorption and Osteolytic Bone Disease in Myeloma", Cancer Research, vol. 67, No. 1, Jan. 1, 2007, pp. 202-208, XP055028421, ISSN: 0008-5472, DOI: 10.1158/0008-5472. CAN-06-1287, abstract, p. 203, right-hand column, paragraph 2.

* cited by examiner

*Primary Examiner* — Xiaozhen Xie
(74) *Attorney, Agent, or Firm* — Banner & Witcoff, Ltd.

(57) ABSTRACT

The present invention relates to a polypeptide for use as a medicament in the treatment and/or prevention of a disease wherein the RANKL-RANK signaling pathway is involved, in particular a bone resorptive disease.

7 Claims, 8 Drawing Sheets

```
                        SEQUENCE LISTING

<160> NUMBER OF SEQ ID NOS: 45

<210> SEQ ID NO 1
<211> LENGTH: 5
<212> TYPE: PRT
<213> ORGANISM: Artificial Sequence
<220> FEATURE:
<223> OTHER INFORMATION: Pep822 binding to the RANK cleft

<400> SEQUENCE: 1

Leu Lys Leu Cys Ser
1               5

<210> SEQ ID NO 2
<211> LENGTH: 9
<212> TYPE: PRT
<213> ORGANISM: Artificial Sequence
```

```
<220> FEATURE:
<223> OTHER INFORMATION: Pep8 binding to the RANK cleft

<400> SEQUENCE: 2

Asn Val Leu Lys Leu Cys Ser Gly Glu
1               5

<210> SEQ ID NO 3
<211> LENGTH: 12
<212> TYPE: PRT
<213> ORGANISM: Artificial Sequence
<220> FEATURE:
<223> OTHER INFORMATION: Pep801 binding to the RANK cleft

<400> SEQUENCE: 3

Glu Leu Ala Asn Val Leu Lys Leu Cys Ser Gly Glu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Pep802 binding to the RANK cleft

<400> SEQUENCE: 4

Asn Val Leu Lys Leu Cys Ser Gly Glu Ala Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Pep803 binding to the RANK cleft

<400> SEQUENCE: 5

Glu Leu Ala Asn Val Leu Lys Leu Cys Ser Gly Glu Ala Tyr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Pep804 binding to the RANK cleft

<400> SEQUENCE: 6

Asn Val Leu Lys Leu Cys Ser Gly Glu Ala Tyr Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Pep805 binding to the RANK cleft

<400> SEQUENCE: 7

Asn Val Leu Lys Leu Ala Cys Ser Gly Glu
1               5                   10

<210> SEQ ID NO 8
<211> LENGTH: 8
<212> TYPE: PRT
<213> ORGANISM: Artificial Sequence
```

-continued

<220> FEATURE:
<223> OTHER INFORMATION: Pep806 binding to the RANK cleft

<400> SEQUENCE: 8

Asn Val Leu Lys Leu Cys Ser Glu
1 5

<210> SEQ ID NO 9
<211> LENGTH: 9
<212> TYPE: PRT
<213> ORGANISM: Artificial Sequence
<220> FEATURE:
<223> OTHER INFORMATION: Pep808 binding to the RANK cleft

<400> SEQUENCE: 9

Asn Val Leu Lys Phe Cys Ser Gly Glu
1 5

<210> SEQ ID NO 10
<211> LENGTH: 9
<212> TYPE: PRT
<213> ORGANISM: Artificial Sequence
<220> FEATURE:
<223> OTHER INFORMATION: Pep809 binding to the RANK cleft

<400> SEQUENCE: 10

Asn Val Ile Lys Leu Cys Ser Gly Glu
1 5

<210> SEQ ID NO 11
<211> LENGTH: 9
<212> TYPE: PRT
<213> ORGANISM: Artificial Sequence
<220> FEATURE:
<223> OTHER INFORMATION: Pep810 binding to the RANK cleft

<400> SEQUENCE: 11

Asn Val Leu Lys Leu Cys His Gly Glu
1 5

<210> SEQ ID NO 12
<211> LENGTH: 10
<212> TYPE: PRT
<213> ORGANISM: Artificial Sequence
<220> FEATURE:
<223> OTHER INFORMATION: Pep811 binding to the RANK cleft

<400> SEQUENCE: 12

Glu Asn Val Leu Lys Leu Cys Ser Gly Glu
1 5 10

<210> SEQ ID NO 13
<211> LENGTH: 9
<212> TYPE: PRT
<213> ORGANISM: Artificial Sequence
<220> FEATURE:
<223> OTHER INFORMATION: Pep812 binding to the RANK cleft

<400> SEQUENCE: 13

Asn Ala Leu Lys Leu Cys Ser Gly Glu
1 5

<210> SEQ ID NO 14
<211> LENGTH: 9
<212> TYPE: PRT
<213> ORGANISM: Artificial Sequence

```
<220> FEATURE:
<223> OTHER INFORMATION: Pep813 binding to the RANK cleft

<400> SEQUENCE: 14

Glu Val Leu Lys Leu Cys Ser Gly Asn
1               5

<210> SEQ ID NO 15
<211> LENGTH: 11
<212> TYPE: PRT
<213> ORGANISM: Artificial Sequence
<220> FEATURE:
<223> OTHER INFORMATION: Pep814 binding to the RANK cleft

<400> SEQUENCE: 15

Asn Ala Leu Lys Leu Cys Ser Gly Glu Met Arg
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Pep815 binding to the RANK cleft

<400> SEQUENCE: 16

Asn Ala Leu Lys Leu Ala Cys Ser Gly Glu
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Pep816 binding to the RANK cleft

<400> SEQUENCE: 17

Asn Ala Leu Lys Leu Phe Cys Ser Gly Glu
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Pep817 binding to the RANK cleft

<400> SEQUENCE: 18

Asn Ala Leu Arg Leu Cys Ser Gly Glu
1               5

<210> SEQ ID NO 19
<211> LENGTH: 9
<212> TYPE: PRT
<213> ORGANISM: Artificial Sequence
<220> FEATURE:
<223> OTHER INFORMATION: Pep818 binding to the RANK cleft

<400> SEQUENCE: 19

Asn Ala Leu His Leu Cys Ser Gly Glu
1               5

<210> SEQ ID NO 20
<211> LENGTH: 9
<212> TYPE: PRT
<213> ORGANISM: Artificial Sequence
```

```
<220> FEATURE:
<223> OTHER INFORMATION: Pep819 binding to the RANK cleft

<400> SEQUENCE: 20

Asn Ala Leu Phe Leu Cys Ser Gly Glu
1               5

<210> SEQ ID NO 21
<211> LENGTH: 9
<212> TYPE: PRT
<213> ORGANISM: Artificial Sequence
<220> FEATURE:
<223> OTHER INFORMATION: Pep820 binding to the RANK cleft

<400> SEQUENCE: 21

Asn Ala Leu Asn Leu Cys Ser Gly Glu
1               5

<210> SEQ ID NO 22
<211> LENGTH: 13
<212> TYPE: PRT
<213> ORGANISM: Artificial Sequence
<220> FEATURE:
<223> OTHER INFORMATION: Pep823 binding to the RANK cleft

<400> SEQUENCE: 22

Tyr Cys Asn Val Leu Lys Leu Cys Ser Gly Glu Cys Tyr
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Pep824 binding to the RANK cleft

<400> SEQUENCE: 23

Asn Ala Leu Lys His Cys Ser Gly Glu
1               5

<210> SEQ ID NO 24
<211> LENGTH: 12
<212> TYPE: PRT
<213> ORGANISM: Artificial Sequence
<220> FEATURE:
<223> OTHER INFORMATION: Pep501 binding to the RANK cleft

<400> SEQUENCE: 24

Glu Leu Ala Ser Phe Leu Lys Ile Ser Gln Leu Gly
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Pep401 binding to the RANK cleft

<400> SEQUENCE: 25

Glu Leu Ala Ser Phe Asn Lys Ile Thr Gln Leu Gly
1               5                   10

<210> SEQ ID NO 26
<211> LENGTH: 12
<212> TYPE: PRT
<213> ORGANISM: Artificial Sequence
```

```
<220> FEATURE:
<223> OTHER INFORMATION: Pep402 binding to the RANK cleft

<400> SEQUENCE: 26

Glu Leu Ala Ser Phe Asn Arg Ile Thr Gln Leu Gly
1               5                   10

<210> SEQ ID NO 27
<211> LENGTH: 13
<212> TYPE: PRT
<213> ORGANISM: Artificial Sequence
<220> FEATURE:
<223> OTHER INFORMATION: PepA17 binding to the RANK cleft

<400> SEQUENCE: 27

Trp Leu Glu Thr Arg Leu Thr Asn His Met Glu Leu Gln
1               5                   10

<210> SEQ ID NO 28
<211> LENGTH: 13
<212> TYPE: PRT
<213> ORGANISM: Artificial Sequence
<220> FEATURE:
<223> OTHER INFORMATION: PepA18 binding to the RANK cleft

<400> SEQUENCE: 28

Ala Lys Phe His Gly Glu Leu Met Ala Asp Gln Trp Gln
1               5                   10

<210> SEQ ID NO 29
<211> LENGTH: 13
<212> TYPE: PRT
<213> ORGANISM: Artificial Sequence
<220> FEATURE:
<223> OTHER INFORMATION: PepA19 binding to the RANK cleft

<400> SEQUENCE: 29

Asn Glu Met Asp Leu Pro Lys Lys Ser Cys Leu Met Asn
1               5                   10

<210> SEQ ID NO 30
<211> LENGTH: 9
<212> TYPE: PRT
<213> ORGANISM: Artificial Sequence
<220> FEATURE:
<223> OTHER INFORMATION: PepA20 binding to the RANK cleft

<400> SEQUENCE: 30

Trp Ala Ala Arg Leu Gly Asp Pro Thr
1               5

<210> SEQ ID NO 31
<211> LENGTH: 12
<212> TYPE: PRT
<213> ORGANISM: Artificial Sequence
<220> FEATURE:
<223> OTHER INFORMATION: Pep1 binding to the RANK cleft

<400> SEQUENCE: 31

Glu Leu Ala Ser Tyr Ile Ile Ile Thr Gln Leu Gly
1               5                   10

<210> SEQ ID NO 32
<211> LENGTH: 5
<212> TYPE: PRT
<213> ORGANISM: Artificial Sequence
```

```
<220> FEATURE:
<223> OTHER INFORMATION: Peptide binding to the RANK cleft
<220> FEATURE:
<221> NAME/KEY: VARIANT
<222> LOCATION: (3)..(3)
<223> OTHER INFORMATION: Xaa is Asp, Phe, His, Ile, Lys, Leu, Gln, Arg,
      Val, Trp or Tyr

<400> SEQUENCE: 32

Leu Lys Xaa Cys Ser
1               5

<210> SEQ ID NO 33
<211> LENGTH: 5
<212> TYPE: PRT
<213> ORGANISM: Artificial Sequence
<220> FEATURE:
<223> OTHER INFORMATION: Peptide binding to the RANK cleft
<220> FEATURE:
<221> NAME/KEY: VARIANT
<222> LOCATION: (3)..(3)
<223> OTHER INFORMATION: Xaa is Phe, His, Ile, Leu, Gln, Arg or Trp

<400> SEQUENCE: 33

Leu Lys Xaa Cys Ser
1               5

<210> SEQ ID NO 34
<211> LENGTH: 21
<212> TYPE: DNA
<213> ORGANISM: Artificial Sequence
<220> FEATURE:
<223> OTHER INFORMATION: Cathepsin K forward primer

<400> SEQUENCE: 34
cccagactcc atcgactatc g                                              21

<210> SEQ ID NO 35
<211> LENGTH: 24
<212> TYPE: DNA
<213> ORGANISM: Artificial Sequence
<220> FEATURE:
<223> OTHER INFORMATION: Cathepsin K reverse primer

<400> SEQUENCE: 35
ctgtaccctc tgcacttagc tgcc                                           24

<210> SEQ ID NO 36
<211> LENGTH: 21
<212> TYPE: DNA
<213> ORGANISM: Artificial Sequence
<220> FEATURE:
<223> OTHER INFORMATION: TRAP forward primer

<400> SEQUENCE: 36
aagactcact gggtggcttt g                                              21

<210> SEQ ID NO 37
<211> LENGTH: 20
<212> TYPE: DNA
<213> ORGANISM: Artificial Sequence
<220> FEATURE:
<223> OTHER INFORMATION: TRAP reverse primer

<400> SEQUENCE: 37
ggcagtcatg ggagttcagg                                                20
```

```
<210> SEQ ID NO 38
<211> LENGTH: 20
<212> TYPE: DNA
<213> ORGANISM: Artificial Sequence
<220> FEATURE:
<223> OTHER INFORMATION: NFATc1 forward primer

<400> SEQUENCE: 38
ggtcttcggg agaggagaaa                                              20

<210> SEQ ID NO 39
<211> LENGTH: 20
<212> TYPE: DNA
<213> ORGANISM: Artificial Sequence
<220> FEATURE:
<223> OTHER INFORMATION: NFATc1 reverse primer

<400> SEQUENCE: 39
tgacgttgga ggatgcatag                                              20

<210> SEQ ID NO 40
<211> LENGTH: 24
<212> TYPE: DNA
<213> ORGANISM: Artificial Sequence
<220> FEATURE:
<223> OTHER INFORMATION: GAPDH forward primer

<400> SEQUENCE: 40
tgggtgtgaa ccatgagaag tatg                                         24

<210> SEQ ID NO 41
<211> LENGTH: 18
<212> TYPE: DNA
<213> ORGANISM: Artificial Sequence
<220> FEATURE:
<223> OTHER INFORMATION: GAPDH reverse primer

<400> SEQUENCE: 41
ggtgcaggag gcattgct                                                18

<210> SEQ ID NO 42
<211> LENGTH: 19
<212> TYPE: DNA
<213> ORGANISM: Artificial Sequence
<220> FEATURE:
<223> OTHER INFORMATION: B2M forward primer

<400> SEQUENCE: 42
ttctggcctg gaggctatc                                               19

<210> SEQ ID NO 43
<211> LENGTH: 23
<212> TYPE: DNA
<213> ORGANISM: Artificial Sequence
<220> FEATURE:
<223> OTHER INFORMATION: B2M reverse primer

<400> SEQUENCE: 43
tcaggaaatt tgactttcca ttc                                          23

<210> SEQ ID NO 44
<211> LENGTH: 18
<212> TYPE: DNA
<213> ORGANISM: Artificial Sequence
<220> FEATURE:
<223> OTHER INFORMATION: ACTB forward primer
```

-continued

```
<400> SEQUENCE: 44
ccaaccgcga gaagatga                                                        18

<210> SEQ ID NO 45
<211> LENGTH: 20
<212> TYPE: DNA
<213> ORGANISM: Artificial Sequence
<220> FEATURE:
<223> OTHER INFORMATION: ACTB reverse primer

<400> SEQUENCE: 45
ccagaggcgt acagggatag                                                      20
```

PEPTIDES TARGETING RECEPTOR ACTIVATOR OF NUCLEAR FACTOR-κB (RANK) AND THEIR APPLICATIONS

The present application is a U.S. National Phase filing of International Application No. PCT/EP2012/076729 filed on Dec. 21, 2012, designating the United States of America and claiming priority to European Patent Application No. 11306766.4, filed on Dec. 23, 2011, and to European Patent Application No. 12305886.9 filed on Jul. 20, 2012; and the present application claims priority to and the benefit of all the above-identified applications, all of which are incorporated by reference herein in their entireties.

FIELD OF THE INVENTION

The present invention relates to the field of prevention and treatment of diseases related to activation of the RANKL-RANK signaling pathway.

In particular, the invention relates to an isolated polypeptide useful for the prevention and treatment of bone resorptive diseases.

BACKGROUND OF THE INVENTION

Bone tissue undergoes constant remodeling to fulfill its principal functions of mechanical support, maintenance of calcium homeostasis, and as a stem cell supplier. This process is mediated by two cell lineages: the hematopoietic bone-resorbing osteoclasts and the bone-forming mesenchymal osteoblasts and osteocytes. Under physiological conditions, the balance between bone formation and resorption is tightly regulated and determines bone density. This balance is based on the RANK/RANKL/OPG pathway.

Receptor activator of nuclear factor-κB (RANK) is a member of the tumor necrosis factor family expressed by osteoclasts and their precursors. The interaction of RANK with RANKL (its ligand) has been identified as the final common pathway through which bone resorption is regulated. By binding to its receptor RANK on osteoclastic precursors, RANKL controls the differentiation, proliferation, and survival of osteoclasts. Osteoprotegerin (OPG) is the natural inhibitor of RANKL. RANK and RANKL are expressed in many regular cell types (Theoleyre et al. 2004) but their activity is the most prominent in bone tissue, skin (Duheron et al. 2011) and mammary glands (Gonzalez-Suarez et al 2010; Schramek et al 2010). RANK-RANKL expression is severely enhanced in non-bone cancer cells such as breast or melanoma cancers, in their associated metastasis (Jones et al. 2006) and in primary bone cancers as in osteosarcoma (Mori et al. 2007).

Disruption of the homeostatic balance can lead to pathologic bone loss, such as in age-related osteoporosis, periodontal disease or inflammatory rheumatoid arthritis, or to excessive bone formation, such as in skeletal malformations linked or not with genetic mutations and/or polymorphisms (Whyte et al. 2009) or to alteration in bone remodeling. Perturbations in the ratio of OPG to RANKL have been demonstrated to occur with estrogen deficiency, hyperparathyroidism, and other disorders that stimulate bone resorption. RANKL is also expressed by lymphocytes and synovial fibroblasts and may mediate bone loss associated with inflammatory conditions.

The discovery of the RANK/RANKL/OPG pathway and its implications in the pathogenesis of bone diseases provided a molecular target for therapies to improve bone health.

The development of small molecules, OPG mimetics which target RANKL have been suggested for the development of therapeutic agents to treat bone diseases, in particular bone resorptive diseases. Cheng and his co-workers (Cheng et al. 2004) have designed such peptides derived from OPG to block RANKL. Their most promising peptide OP3-4 was able to directly bind RANKL with a measurable interaction by surface plasmon resonance. This interaction was sufficient to reduce in vitro osteoclastogenesis and protect mice in vivo from bone loss.

Another approach initiated by Takasaki in 1997 (Takasaki et al. 1997) was to design bio-compatible molecules able to target RANKL based on peptides derived from the RANK sequence. Their work, initially targeting the TNF-alpha/TNFR interaction, proved useful to block the RANKL/RANK interaction in a TNF-independent way (Aoki et al. 2006). Their most effective peptide named WP9QY was able to inhibit in vitro osteoclastogenesis in a dose-dependent manner and prevent in vivo bone loss in a mouse osteoporosis-induced model.

These peptides were derived from the native sequence of the partner they were targeting, based on assumptions made upon models based on other members of the TNF/TNF-R family: i.e. OP3-4 was selected from the putative OPG-RANKL interface (the model for OPG used TNFR, Fas and TRAIL crystallographic structures) and WP9QY was selected from the putative RANKL-RANK interface (models were based on the TNF-R/TNF-β crystallographic structure). Although their biological activity showed promising results in in vitro and in vivo models, their therapeutic interest was potentially limited by their relatively low binding affinity to RANKL, in comparison to the binding of RANKL to RANK.

Over the past decade, there have been tremendous advances in the management of metabolic bone disorders with the introduction of novel bone-chelating agents (zoledronate being the most prominent treatment to date) and the development of a monoclonal antibody (denosumab) directed against RANKL (Baron et al. 2011). Although these therapies show promising improvements in the treatment of bone diseases, in particular in bone resorptive diseases, their application is limited by the poor bioavailability and/or stability of large macromolecules, such as antibodies or chimeras, the mode of administration, the high cost and the risk of mild to severe and sometimes even life-compromising side effects, such as skin rashes, immunogenicity, osteonecrosis of the jaw or increased trabecular bone mineral density leading to growth retardation.

There remains, therefore, a significant need for new and improved compounds for the prevention and/or treatment of bone diseases, in particular of bone resorptive diseases, which are effective in inhibiting osteoclastogenesis, cheap to produce, possess a high bioavailability, which may be easily administered to patients while being without severe side effects. The present inventors have made a significant step forward with the invention disclosed herein.

DETAILED DESCRIPTION OF THE INVENTION

The purpose of the invention is to fulfill this need by providing new polypeptides, which make it possible to solve in whole or part the problems mentioned above.

The inventors have designed innovative peptides which are able to specifically bind the receptor RANK and have a strong inhibitory effect on osteoclastogenesis. Contrary to the peptides developed so far, the peptide sequences of the invention are not derived from the existing RANK, RANKL or OPG amino acid sequences and are not present in any natural protein or peptide known in the literature.

In one aspect, the invention relates to an isolated polypeptide consisting of a sequence of up to 20 amino acids, wherein said sequence comprising or consisting of a sequence selected from the group consisting of:
SEQ ID NO: 32; and
a sequence having at least 80% of identity with SEQ ID NO: 32 over the entire length of SEQ ID NO: 32;
in particular:
SEQ ID NO: 33; and
a sequence having at least 80% of identity with SEQ ID NO: 33 over the entire length of SEQ ID NO: 33;
more particularly:
SEQ ID NO: 1 (LKLCS); and
a sequence having at least 80% of identity with SEQ ID NO: 1 over the entire length of SEQ ID NO: 1;
for use as a medicament in the treatment and/or prevention of a bone disease, in particular a bone resorptive disease.

The polypeptide according to the invention has in particular the following advantages:
It has a strong inhibitory effect on osteoclastogenesis;
It has no severe side effects. In particular, it has no obvious cytotoxicity or pro-apoptotic activities;
It is cheap to produce;
It possesses a high bioavailability;
It has a high capacity to penetrate tumors. As illustrated in the article of Lien et al. (2003), it is well known in the art that in the treatment of cancer, a further advantage of peptides over larger proteins such as full length antibodies is their superior ability to penetrate tumors;
It proved to be very stable over time which possibly elicits its administration to patients via any existing delivery technique.

Unless defined otherwise, all technical and scientific terms used herein have the same meaning as commonly understood to one skilled in the relevant art.

For convenience, the meaning of certain terms and phrases employed in the specification, examples and claims are provided.

As used herein, the term "bone resorptive disease" refers to any disease wherein bone homeostasis is altered through the RANKL-RANK signaling pathway. The homeostasis imbalance may appear in non-inflammatory or in inflammatory bone resorptive diseases, in oncologic or in non-oncologic bone resorptive diseases as described in the article of Theoleyre et al. (2004).

In a non-inflammatory context, bone resorptive diseases include metabolic bone diseases such as osteoporosis (including type I (postmenopausal) and type II (senile) osteoporosis), skeletal malformations linked or not with genetic mutations and/or polymorphisms (Whyte et al. 2009), vitamin D deficiency such as observed in rachitism, any disease caused by any treatment having as a side effect altered bone remodeling (including endocrine therapies such as tamoxifen or aromatase inhibitors (Lee et al. 2011), glucocorticoid-induced osteoporosis (Hansen et al. 2011), hypercalcemia of malignancy), osteolytic bone diseases (benign tumors such as multiple myeloma or giant-cell tumor of bone (Croucher et al. 2001) or bone sarcomas (Dai et al. 2011)).

Postmenopausal osteoporosis (also called PMO or type I osteoporosis) is primarily due to estrogen deficiency.

Senile osteoporosis (also called type II osteoporosis) is primarily due to an aging skeleton and calcium deficiency.

Glucocorticoid-induced osteoporosis is a form of osteoporosis that is caused by taking glucocorticoid medications such as prednisone (Deltasone, Orasone, etc.), prednisolone (Prelone), dexamethasone (Decadron, Hexadrol), and cortisone (Cortone Acetate).

In an inflammatory context, bone resorptive diseases include all arthritis pathologies such as rheumatoid arthritis, osteolytic bone diseases, periodontal diseases and any cardiovascular disease wherein the RANKL-RANK pathway is involved such as atherosclerosis and fractures.

In the oncologic context, bone resorptive diseases include:
primary bone cancers such as osteosarcoma, Ewing's sarcoma, chondrosarcoma, and benign bone cancers such as multiple myeloma or giant-cell bone tumor (Dai et al. 2011; Croucher et al. 2001);
primary cancers wherein the RANKL-RANK signaling pathway is a direct enhancer of the tumor growth, such as breast cancer (Jones et al. 2006; Schramek et al. 2010; Gonzalez-Suarez 2010), multiple myeloma (Demchenko and Kuehl 2010), carcinoma, neuroblastoma, chondroblastoma, colorectal cancer, renal cancer, esophageal cancer, hepatic cancer, cervical cancer, endometrial cancer (Theoleyre et al. 2004; Santini et al. 2011);
secondary bone cancers also described as skeletal metastasis, following a primary cancer including prostate cancer, breast cancer (Schramek et al. 2010; Gonzalez-Suarez 2010), lung cancer, colorectal cancer, renal cancer, esophageal cancer, bladder cancer, hepatic cancer, cervical cancer, endometrial cancer, salivary glands cancer, squamous cancer, malignant melanoma (Smith 2011; Santini et al. 2011)

As used herein, the term "primary bone cancer" refers to any cancer which originates in a bone. Primary bone cancers include but are not limited to osteosarcoma (also called osteogenic sarcoma), Ewing's sarcoma, chondrosarcoma.

As used herein, the term "secondary bone cancer" refers to any skeletal metastasis following a primary cancer including prostate cancer, breast cancer, lung cancer, colorectal cancer, renal cancer, esophageal cancer, bladder cancer, hepatic cancer, cervical cancer, endometrial cancer, salivary glands cancer, squamous cancer, malignant melanoma. Secondary bone cancer is the result of cancer cells spreading to the bone from a primary tumor.

In particular, bone resorptive diseases are selected from the group consisting of osteoporosis, osteolytic bone disease, primary bone cancers, secondary bone cancers, periodontal disease and rheumatoid arthritis.

More particularly, bone diseases are selected from the group consisting of osteoporosis, primary bone cancers, secondary bone cancers and rheumatoid arthritis.

In particular, the isolated polypeptide according to the invention consisting of a sequence of up to 19 amino acids, more particularly of up to 18, 17, 16, 15, 14, 13, 12, 11, 10, 9, 8, 7, 6, 5 and even more particularly of up to 9, 8, 7, 6, 5 amino acids.

In particular, the isolated polypeptide according to the invention consisting of a sequence of up to 20 amino acids and at least 5 amino acids, more particularly at least 6 amino acids and even more particularly at least 7, 8, 9, 10, 11, 12, 13, 14, 15, 16, 17, 18, 19 amino acids.

In particular, the isolated polypeptide according to the invention consisting of a sequence of 5 to 20 amino acids, more particularly 5 to 19 amino acids and even more particularly 6 to 18, 7 to 17, 8 to 16, 9 to 15, 10 to 14, 11 to 13 amino acids.

In particular, the isolated polypeptide according to the invention, more particularly the isolated polypeptide consisting of a sequence comprising or consisting of a sequence having at least 80% of identity with SEQ ID NO: 32, SEQ ID NO: 33 or SEQ ID NO: 1 over the entire length of SEQ ID NO: 32, SEQ ID NO: 33 or SEQ ID NO: 1 respectively, have the ability to inhibit RANKL-induced osteoclastogenesis.

The ability of a polypeptide to inhibit RANKL-induced osteoclastogenesis can be determined by one skilled in the art by tests including assessment of the effect of polypeptide on osteoclast differentiation as described in the articles of Baud'Huin et al. 2009 and Duplomb et al. 2008.

In particular, the isolated polypeptide according to the invention consisting of a sequence comprising or consisting of a sequence having at least 80%, more particularly at least 85%, at least 86%, at least 87%, at least 88%, at least 89%, at least 90%, at least 91%, at least 92%, at least 93%, at least 94%, at least 95%, at least 96%, at least 97%, at least 98% and even more particularly at least 99% of identity with SEQ ID NO: 32, SEQ ID NO: 33 or SEQ ID NO: 1 over the entire length of SEQ ID NO: 32, SEQ ID NO: 33 or SEQ ID NO: 1 respectively.

In particular, the isolated polypeptide according to the invention consisting of a sequence comprising or consisting of a sequence having at least 80%, more particularly at least 85%, at least 86%, at least 87%, at least 88%, at least 89%, at least 90%, at least 91%, at least 92%, at least 93%, at least 94%, at least 95%, at least 96%, at least 97%, at least 98% and even more particularly at least 99% of identity with SEQ ID NO: 1 over the entire length of SEQ ID NO: 1.

The percentages of identity to which reference is made in the presentation of the present invention are determined on the basis of a global alignment of sequences to be compared, that is to say, on an alignment of sequences over their entire length, using for example the algorithm of Needleman and Wunsch 1970. This sequence comparison can be done for example using the needle software by using the parameter "Gap open" equal to 10.0, the parameter "Gap Extend" equal to 0.5, and a matrix "BLOSUM 62". Software such as needle is available on the website ebi.ac.uk worldwide, under the name "needle".

In particular, the isolated polypeptide according to the invention consisting of a sequence comprising or consisting of a sequence selected from the group consisting of:
SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 32 and SEQ ID NO: 33, more particularly, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 11, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 21, and SEQ ID NO: 23, even more particularly SEQ ID NO: 1, SEQ ID NO: 2, SEQ ID NO: 3, SEQ ID NO: 4, SEQ ID NO: 6, SEQ ID NO: 9, SEQ ID NO: 11, SEQ ID NO: 12, SEQ ID NO: 14, SEQ ID NO: 19, SEQ ID NO: 20 SEQ ID NO: 21 and SEQ ID NO: 23 even more particularly SEQ ID NO: 1, SEQ ID NO: 2, SEQ ID NO: 4, SEQ ID NO: 9, SEQ ID NO: 12 and SEQ ID NO: 20, even more particularly SEQ ID NO: 1, SEQ ID NO: 2, SEQ ID NO: 9 and SEQ ID NO: 20 and even more particularly SEQ ID NO: 2.

In particular, the isolated polypeptide according to the invention consisting of a sequence selected from the group consisting of:
SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 32 and SEQ ID NO: 33, more particularly, SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 9, SEQ ID NO: 11, SEQ ID NO: 12, SEQ ID NO: 13, SEQ ID NO: 14, SEQ ID NO: 16, SEQ ID NO: 17, SEQ ID NO: 18, SEQ ID NO: 19, SEQ ID NO: 20, SEQ ID NO: 21, and SEQ ID NO: 23, even more particularly SEQ ID NO: 1, SEQ ID NO: 2, SEQ ID NO: 3, SEQ ID NO: 4, SEQ ID NO: 6, SEQ ID NO: 9, SEQ ID NO: 11, SEQ ID NO: 12, SEQ ID NO: 14, SEQ ID NO: 19, SEQ ID NO: 20 SEQ ID NO: 21 and SEQ ID NO: 23 even more particularly SEQ ID NO: 1, SEQ ID NO: 2, SEQ ID NO: 4, SEQ ID NO: 9, SEQ ID NO: 12 and SEQ ID NO: 20, even more particularly SEQ ID NO: 1, SEQ ID NO: 2, SEQ ID NO: 9 and SEQ ID NO: 20 and even more particularly SEQ ID NO: 2.

In particular, the isolated polypeptide according to the invention contains at least one biochemical modification selected from the group consisting of pegylation, acetylation, formylation, myristic acid addition, palmytoylation, benzyloxycarbonylation, amidation, succinylation, glycosylation, in particular pegylation.

In particular, the isolated polypeptide according to the invention comprises at least one polyethylene glycol group, more particularly at least 2, at least 3, at least 4, at least 5, at least 6, at least 7, at least 8, at least 9, at least 10, polyethylene glycol groups, in a linear, branched or more complex organization.

The pegylation of the polypeptide of the invention has the advantage that it optimizes the polypeptide solubility, bioavailability and stability and decreases the immunogenicity.

In particular, the isolated polypeptide according to the invention comprises less than 20 polyethylene glycol groups, more particularly less than 19, less than 18, less than 17, less than 16, less than 15, less than 14, less than 13, less than 12 and even more particularly less than 11 polyethylene glycol groups.

In particular, the isolated polypeptide according to the invention comprises 1 polyethylene glycol group per amino acid.

Said polyethylene group can be attached to any appropriate amino acid suitable for modification of the polypeptide of the invention. In particular, at least one polyethylene glycol group is attached to the N-terminal amino acid or to the C-terminal of said polypeptide. More particularly, at least one polyethylene glycol group is attached to the N-terminal amino acid of said polypeptide.

Particularly, the isolated polypeptide according to the invention comprises 5 or 8 polyethylene glycol groups, in particular in a linear organization, attached to the N-terminal amino acid of said polypeptide.

The invention also relates to an isolated polypeptide according to the invention as described above. The advantageous embodiments are as defined above.

In particular, the isolated polypeptide according to the invention consisting of the amino acid sequence set forth in SEQ ID NO: 2.

The present invention encompasses polypeptides as described above having modified amino acid sequences. Modifications can include but are not limited to amino acid insertions, deletions, substitutions, truncations, fusions, cyclization, disulfide bridging, substitution of D-amino acids by L-amino acids or by beta peptides, modifications to improve cell-membrane pass-through (for instance using a signal peptide or a fragment of Antennapedia homeodomain, Derossi et al. 1994; May et al. 2000) provided that the polypeptides retain the ability to inhibit RANKL-induced osteoclastogenesis. Such modifications may be undertaken to improve polypeptide half-life or biological activity.

The polypeptides according to the invention can be synthesized using conventional methods including chemical synthesis and synthesis using nucleic acid molecules encoding said polypeptides.

The invention also relates to an isolated nucleic acid molecule encoding an isolated polypeptide according to the invention.

In particular, the nucleic acid molecule according to the invention can be operatively linked to a promoter for a eukaryotic DNA dependent RNA polymerase, preferably for RNA polymerase II. If tissue-specific RNA polymerase II promoters are used, the polypeptide of the invention can be selectively expressed in the targeted tissues/cells.

Said promoter can be a constitutive promoter or an inducible promoter well known by one skilled in the art. The promoter can be developmentally regulated, inducible or tissue specific.

In particular, the nucleic acid molecule according to the invention can be operatively linked to an extracellular signal sequence. Said extracellular signal sequence can encode a signal peptide allowing the secretion of the polypeptide of the invention in the extracellular medium. Extracellular signal sequences are well known by one skilled in the art and can encode as an example the signal peptide having the following sequence "MAPRARRRPLFALLLLCALLARLQVALQ" (hRANK signal peptide) (Petersen et al. 2011).

The invention also relates to a vector comprising a nucleic acid molecule according to the invention. Said vector can be appropriated for semi-stable or stable expression.

Particularly, said vector according to the invention is a cloning or an expression vector.

The vectors can be viral vectors such as bacteriophages or non-viral such as plasmids.

The invention also relates to a host cell comprising a nucleic acid molecule according to the invention or a vector according to the invention.

The host cell according to the invention can be useful for production of a polypeptide according to the invention.

The invention also relates to a pharmaceutical composition comprising at least one compound selected from the group consisting of an isolated polypeptide according to the invention, an isolated nucleic acid molecule according to the invention and a vector according to the invention. The advantageous embodiments are as defined above.

The terms "medicament" and "pharmaceutical composition" are used interchangeably and in their broadest sense herein.

Such compound (in particular selected from the group consisting of an isolated polypeptide according to the invention, an isolated nucleic acid molecule according to the invention and a vector according to the invention) can be present in the pharmaceutical composition according to the invention in a therapeutically effective amount (active and non-toxic amount). A therapeutically effective amount refers to that amount of compound which ameliorates the symptoms or condition. Therapeutic efficacy and toxicity may be determined by standard pharmaceutical procedures in cell cultures or experimental animals, e.g., ED50 (the amount therapeutically effective in 50% of the population) and LD50 (the dose lethal to 50% of the population). The amount ratio of toxic to therapeutic effects is the therapeutic index and it can be expressed as the ratio, LD50/ED50. Pharmaceutical compositions which exhibit large therapeutic indices are preferred.

For example, the polypeptide according to the invention, particularly the polypeptide consisting of the sequence set forth in SEQ ID NO: 2, can be administered to a patient, in particular by injection, in an amount within the range from 0.1 to 100 mg/kg of body weight of said patient daily, particularly within the range from 0.5 to 50 mg/kg of body weight of said patient daily and even more particularly within the range from 0.5 to 10 mg/kg of body weight of said patient daily. Said doses will be adjusted to elicit a therapeutic response yet able to protect from a potential immunogenicity of the peptide (Toes et al. 1998).

The pharmaceutical composition according to the invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, the pharmaceutical composition of the invention may contain suitable pharmaceutically acceptable carriers comprising excipients and auxiliaries, which facilitate processing of the active compounds into preparations which can be used pharmaceutically. In particular, the pharmaceutical composition according to the invention is formulated in a pharmaceutical acceptable carrier. Pharmaceutical acceptable carriers are well known by one skilled in the art. Further details on techniques for formulation and administration may be found in the latest edition of Remington's Pharmaceutical Sciences (Maack Publishing Co., Easton, Pa.).

In particular, the pharmaceutical acceptable carrier is a biomaterial.

As used herein the term "biomaterial" refers to any material that is biocompatible, in particular designed to interact with biological systems.

The biomaterial has the advantage that it may precisely determine the initial delivery zone of the polypeptide of the invention, in particular the polypeptide consisting of the sequence set forth in SEQ ID NO: 2, in order to enhance its local efficacy and bioavailability, in a time and/or dose controlled way.

The biomaterial can be selected from the group consisting of phosphocalcic ceramics (e.g. hydroxyapatite (HAP) and beta-tricalcium phosphate), polymers (e.g. copolymers of lactic acid and glycolic acid, hydrogels), materials of natural origin (e.g. cellulose, collagen), particularly phosphocalcic ceramics and even more particularly phosphocalcic ceramics consisting of 40% beta-tricalcium phosphate and 60% hydroxyapatite.

Hydroxyapatite (HAP) and tricalciumphosphate (in particular beta-tricalcium phosphate) ceramics have the advantage to be bioresorbable and osteoconductive.

Pharmaceutical composition suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

The invention also relates to a method for the treatment and/or prevention of a bone resorptive disease comprising the step of administering to a patient in need thereof a therapeutically effective amount of at least one compound selected from the group consisting of an isolated polypeptide according to the invention, an isolated nucleic acid molecule according to the invention and a vector according to the invention. The advantageous embodiments are as defined above.

The invention also relates to a method of inhibiting osteoclastogenesis comprising the step of administering to a patient in need thereof, in particular to a patient having a bone disease and more particularly to a patient having a bone resorptive disease, a therapeutically effective amount of at least one compound selected from the group consisting of an isolated polypeptide according to the invention, an isolated nucleic acid molecule according to the invention and a vector according to the invention. The advantageous embodiments are as defined above.

The invention also relates to an isolated polypeptide according to the invention for use as a medicament. The advantageous embodiments are as defined above.

The invention also relates to an isolated nucleic acid molecule according to the invention for use as a medicament. The advantageous embodiments are as defined above.

The invention also relates to a vector according to the invention for use as a medicament. The advantageous embodiments are as defined above.

The invention also relates to the use of an isolated polypeptide according to the invention for the preparation of a medicament for the treatment and/or prevention of a bone disease, in particular a bone resorptive disease. The advantageous embodiments are as defined above.

The invention also relates to the use of an isolated nucleic acid molecule according to the invention for the preparation of a medicament for the treatment and/or prevention of a bone disease, in particular a bone resorptive disease. The advantageous embodiments are as defined above.

The invention also relates to the use of a vector according to the invention for the preparation of a medicament for the treatment and/or prevention of a bone disease, in particular a bone resorptive disease. The advantageous embodiments are as defined above.

The invention also relates to a combination product comprising:
at least one compound selected from the group consisting of an isolated polypeptide according to the invention, an isolated nucleic acid molecule according to the invention and a vector according to the invention; and
another bone anti-resorptive agent,
for simultaneous, separate or sequential use as a medicament.

The advantageous embodiments are as defined above.

As used herein the term "bone anti-resorptive agent" refers to any agent able to inhibit bone-resorption.

In particular, said another bone anti-resorptive agent is selected from the group consisting of:
anabolism enhancers, in particular selected from the group consisting of parathyroid hormone, BMP2, vitamin D, prostaglandin E2, anti-inflammatory agents; and
catabolism inhibitors, in particular selected from the group consisting of bisphosphonates, cathepsin K inhibitors, p38 inhibitors, JNK inhibitors, IKK inhibitors, NF-κB inhibitors, calcineurin inhibitors, NFAT inhibitor, PI3K inhibitor (Tanaka et al. 2005).

As used herein, the term "catabolism inhibitors" refers to any agent able to protect from bone destruction (Xu et al. 2010).

As used herein, the term "anabolism enhancers" refers to any agent able to restore normal bone mineral density (Boyce et al. 2006).

The invention also relates to a combination product comprising:
at least one compound selected from the group consisting of an isolated polypeptide according to the invention, an isolated nucleic acid molecule according to the invention and a vector according to the invention; and
an anti-tumoral agent,
for simultaneous, separate or sequential use as a medicament.

As used herein, the term <<anti-tumoral agent>> refers to any agent able to prevent and/or treat a cancer, alone or in combination with another agent.

In particular, said anti-tumoral agent is able to prevent and/or treat a primary bone cancer and/or a secondary bone cancer.

In particular, said anti-tumoral agent can be selected in the group consisting of:
actinomycin-D, bleomycin, cisplatin, cyclophosphamide, dactinomycin, doxorubicin, etoposide, gemcitabine, ifosfamide, methotrexate (and highdose methotrexate with leucovorin calcium rescue), paclitaxel, vincristine (Dai et al. 2011; Wittig et al. 2002).

The invention also relates to a combination product according to the invention, for its use in the treatment and/or prevention of a bone resorptive disease, in particular a bone resorptive disease selected from the group consisting of:
osteoporosis, osteolytic bone disease, primary bone cancers, secondary bone cancers, periodontal disease and rheumatoid arthritis.

The advantageous embodiments are as defined above.

Figure 1:
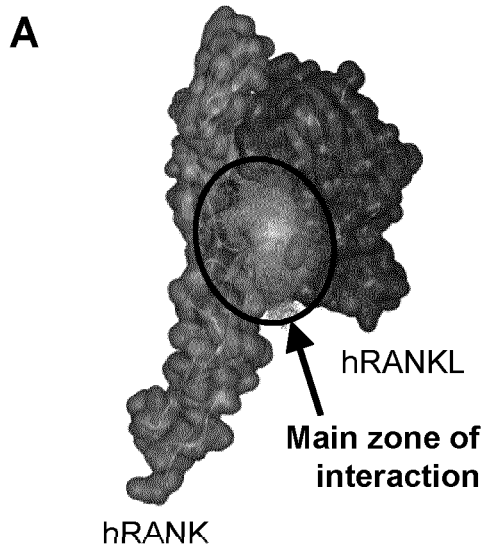
FIG. 1 (A-C) represents the development of small polypeptides inhibiting RANK/RANKL activity. (A) Three-dimensional structure of the RANK-RANKL dimer and main zone of polypeptide interaction from molecular modeling. (B) Effect of inhibitor polypeptide targeting RANK on osteoclast differentiation. CD14+ monocytes were treated with M-SCF (25 ng/ml) and human RANKL (100 ng/ml) in the presence or absence of each polypeptide (50 When osteoclasts had formed, cells were fixed and stained for TRAP, and the TRAP+ multinucleated cells (MNCs) were counted. Results are expressed as percentage of TRAP+ cells in cultures without the corresponding polypeptide. The RANKL-targeting polypeptides WP9QY and OP3-4, as well as the RANKL decoy receptor OPG (50 ng/ml) were used as positive controls. Results are expressed as means±SD of three experiments carried out in triplicate. *$P<0.005$ and #$P<0.05$. (C) The affinity of polypeptide binding to RANK (here, Pep1 (SEQ ID NO: 31)) was measured by Surface plasmon resonance (Biacore) analysis. The sensorgram shows the relative response in resonance units after background subtraction vs. time in seconds. Binding of Pep1 to hRANK is shown at concentrations indicated in the graph. Pep1 binds RANK with a $K_d$ of 20.6 µM ($k_{on}=1.35 \cdot 10^1$ M$^{-1}$s$^{-1}$, $k_{off}=2.78 \cdot 10^{-4}$ s$^{-1}$).
Figure 1:
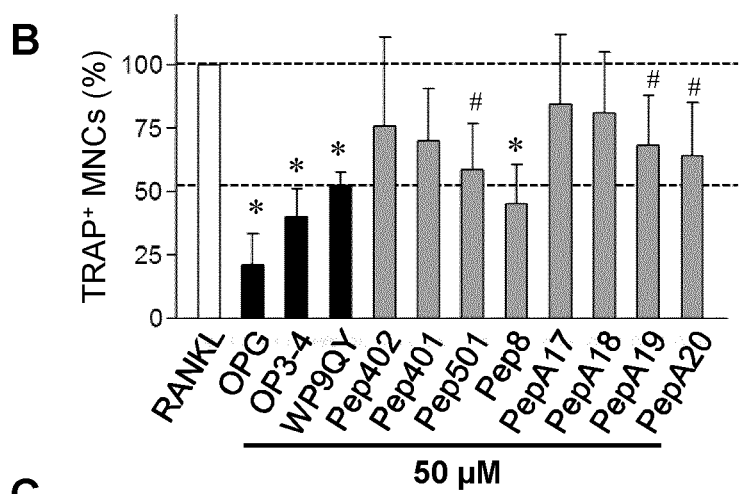
Figure 1:
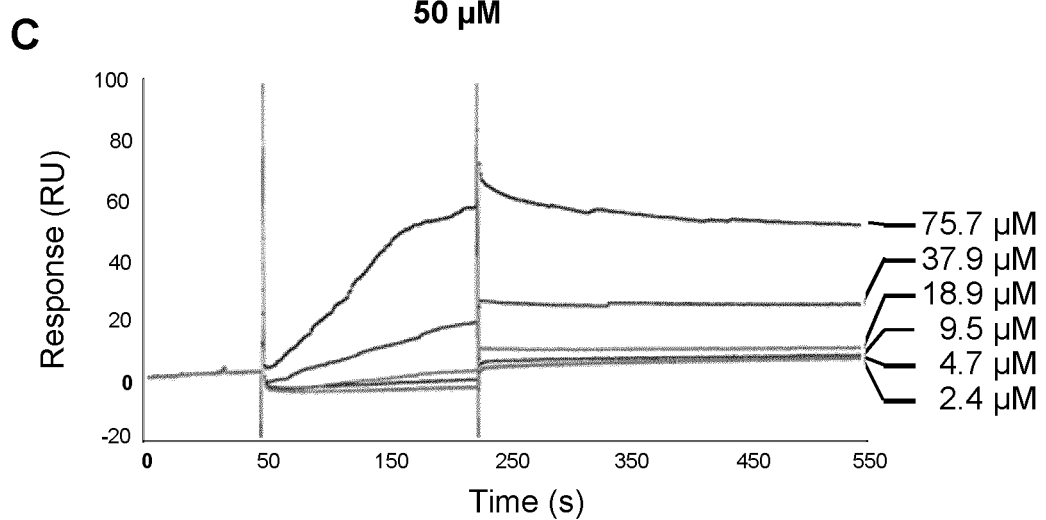

The present invention will be explained in detail with examples in the following text, but the technical scope of the present invention is not limited to these examples.

EXAMPLES

I. Material and Methods

I.1 Generation of a Large Collection of Polypeptides

A wide database of polypeptides filtered for aqueous solubility was generated using in-house bioinformatics tools. Briefly, random amino acids sequences of desired length (7-13 amino acids) were generated in silico and the resulting polypeptide sequences were filtered according to a combination of biochemical and sequence-related filters to ensure most resulting polypeptides will be soluble in vitro and in vivo with most common solvents ($H_2O$, PBS, DMSO/$H_2O$). The resulting collection was processed to provide the three-dimensional coordinates of the polypeptide. Each polypeptide was further typed with the CHARMm force-field (Brooks et al. 1983) to be suitable for further analysis within Discovery Studio 2.5.5 (Accelrys Software Inc, San Diego, Calif., USA).

I.2 Docking Experiments and Refinement of Docking Poses

The Human RANK-RANKL crystal structure (PDB id: 3ME2, Liu et al. 2010) was used as a reference to define putative binding sites at the RANK-RANKL interaction site. The binding of RANKL induces a 36° switch of the two cysteine-rich domains (CRD) in N-terminal of RANK (Liu et al. 2010). The inventors defined the hinge region between the first two and the last two CRDs on RANK as the most favorable binding pocket for docking studies since they contain critical contacts for RANKL-binding (Ta et al. 2010). Docking experiments were performed using the CDOCKER module (Wu et al. 2003) of Discovery Studio 2.5.5. Principal poses were visually inspected and the most promising poses were refined for a better characterization of the most favorable RANK-polypeptide interactions.

I.3 Surface Plasmon Resonance Binding Assays

Biosensor experiments were carried out on a BIAcore 3000 instrument (BIAcore) as published previously (Baud'Huin et al. 2009). Recombinant purified RANKL (2 µg/mL in 5 mM maleate, pH 5.75) or RANK-Fc carrier-free (5 µg/mL in sodium acetate buffer, pH 5.0) were covalently immobilized to the dextran matrix of a CM5 sensor chip (BIAcore) at a flow rate of 5 µL/min. Immobilization levels ranging from 400 to 3000 Response Units (RU) for RANKL or 5000 RU for RANK were obtained. Binding assays were performed at 25° C. in 10 mM Hepes buffer, pH 7.4. The association phase was 180 seconds followed by a dissociation phase in the same buffer. Polypeptides binding studies to RANK or RANKL were determined using single cycle kinetics, starting with 100 µM of the polypeptide of interest followed by 2-fold serial dilutions (ranging from 100 to 0.78 µM). The sensorgrams were fitted to calculate the equilibrium-dissociation constants using the Langmuir 1:1 model with BiaEval 4.1 software (BIAcore). RANK-Fc CF, RANKL and OPG carrier-free were obtained from R&D Systems (Minneapolis, Minn., USA).

I.4 NMR Spectroscopy

NMR experiments were run at 500.13 MHz for $^1$H on a Bruker AVANCE 500 spectrometer with a Linux PC workstation, using standard 5 mm or Shigemi 3 mm tubes with susceptibility matched to solvent $^2H_2O$/Water sample tubes. The spectra of the polypeptide Pep8 at 0.1, 0.2, 0.4 or 1 mM sample concentrations were recorded in 50 mM sodium phosphate buffer at pH 7.4, prepared in 95% $H_2O$ and 5% $^2H_2O$. Two-dimensional NMR spectra were recorded in the phase-sensitive mode using the States—TPPI method (States et al. 1982). All experiments were carried out using the WATERGATE pulse sequence for water suppression (Piotto et al. 1992) or using the excitation sculpting water suppression (Hwang et al. 1995) to eliminate solvent signal in $H_2O/^2H_2O$ 95:5 solution. The two-dimensional COSY, TOCSY and NOESY spectra were recorded at 280 K. TOCSY spectra were recorded using a MLEV-17 spin-lock sequence (Bax et al. 1985) with a mixing time (τm) of 35 and 70 ms, respectively. 2D NOESY experiments were recorded at a mixing time (τm) of 100, 200 or 500 ms. The heteronuclear spectra $^1$H-$^{13}$C HSQC were recorded at 280 K in the same conditions. For NMR experiments with soluble RANK receptor-Fc (R&D Systems), ligand to protein ratio was ranged from 100:1 to 1000:1 (0.1 to 1 mM Pep8, 1 µM RANK receptor-Fc protein). Chemical shift assignments refer to internal 3-(trimethylsilyl)propionic acid-2,2,3,3-d4, sodium salt (TSP-d4). Transferred nuclear Overhauser effect (TRNOESY) spectra of Pep8 with RANK receptor-Fc protein were recorded using a mixing time (Tm) of 100, 200 or 500 ms.

$^1$D $^1$H STD NMR spectra of the polypeptide—protein mixtures were recorded at 500 MHz with 4K scans and selective saturation of protein resonances as described previously (Pons et al. 2011). The saturation transfer is prone to be reduced due to the low efficiency of the spin diffusion effect in low molecular weight protein (48 kDa). In order to achieve a better saturation transfer efficiency, clean STD-NMR experiments were also performed (Xia et al. 2010) with RF irradiation frequency values at −0.4/10.1/60 ppm ($f_{on1}/f_{on2}/f_{off}$). The height of Gaussian-shaped pulses was set to 200 Hz and the near ligand resonances were >500 Hz. The sensitivity enhancement in STD experiments could be achieved through optimized excitation 90° E-Burp-1 selective pulse or 90° E-Burp-1 cosine modulated selective pulse (Cutting et al. 2007). Interestingly, the combination of the Clean STD-NMR with 90° E-Burp-1 cosine modulated selective pulses gives better signal to noise ratio. The relative STD values observed were similar to the classical STD-NMR experiment.

Subtraction of FID values with on- and off-resonance protein saturation was achieved by phase cycling. Relative STD values were calculated by dividing STD signal intensities by the intensities of the corresponding signals in a one-dimensional $^1$H NMR reference spectrum of the same sample recorded with similar parameter conditions.

I.5 Polypeptides and Reagents

All polypeptides and pegylated polypeptides (pegylations were carried out with two different linear chain lengths, $(PEG)_5$ and $(PEG)_8$) delivered with >95% purity (HPLC) were purchased from GeneCust EUROPE (Dudelange, Luxembourg). Polypeptides were stored at −20° C. until use. For in vitro experiments, 1 mM stock solutions were prepared in phosphate buffered saline (PBS) or cell culture medium and stored at −20° C. for up to two weeks. For hydrophobic polypeptides, stock solutions containing 1-5% DMSO (v/v) were prepared. For in vivo experiments with polypeptide Pep8 (Pep8), a 2.5 mg/mL solution in PBS was freshly prepared and sterile filtered before use.

I.6 Osteoclast Differentiation Assays

Human peripheral blood mononuclear cells (PBMCs) were isolated by centrifugation over Ficoll gradient (Sigma, Saint Quentin Fallavier, France). CD14$^+$ cells were magnetically labeled with CD14 Microbeads and positively selected by MACS technology (Miltenyi Biotec, Paris, France) as described previously (Duplomb et al. 2008). CD11b$^+$ monocytes were purified from murine bone marrow cells obtained by flushing the bone marrow from femora and tibiae of 4-week-old C57BL6 male mice, using MACS microbeads (Baud'huin et al. 2010). The purity of cell preparations was around 96%, as controlled by flow cytometry. Generation of osteoclasts from human CD14$^+$ and murine CD11b$^+$ monocytes was performed as described previously (Duplomb et al. 2008, Baud'huin et al. 2010). Briefly, purified cells were cultured in α-minimum essential medium (α-MEM, Gibco/Invitrogen, USA) with 10% fetal calf serum and 25 ng/mL human/murine macrophage colony-stimulating factor (M-CSF, R&D Systems, Abingdton, UK). After 3 days of culture, cell medium was replaced by fresh medium containing M-CSF and recombinant human RANKL (100 ng/mL, R&D system), supplemented with or without a polypeptide of interest (0.5-100 μM) or 50 ng/mL human OPG (R&D Systems) used as a reference inhibitor. Soluble cytokines, receptor and polypeptides were renewed every 3 days until multinucleated osteoclasts had formed. After 12 days of culture for CD14$^+$ cells and 15 days for CD11b$^+$ cells, osteoclasts were visualized by TRAP staining (Sigma, France) and cells formed with three or more nuclei were manually counted and analyzed statistically.

I.7 RNA Isolation and Real-Time PCR

Total RNA from CD14$^+$ cells treated with Pep8 (25 or 50 μM) in the presence or absence of RANKL (100 ng/mL), was extracted using the Nucleospin RNA II kit (Macherey-Nagel, Duren, Germany) according to the manufacturer's instructions. Untreated cells cultured with or without RANKL served as controls. First-strand cDNA was synthesized from 5 μg total CD14$^+$ RNA with ThermoScript™ RT (Invitrogen, Saint Aubin, France) and oligo(dT) primers, according to the manufacturer's recommendations. Quantitative real-time PCR (qPCR) was carried out on a Chromo4™ System (Biorad, Marnes-la-Coquette, France) with a reaction mix containing 15-40 ng reverse-transcribed total RNA, 300 nM primers and 2× SYBR green buffer (Biorad). Analysis was performed according to the method described by Vandesompele et al. (Vandesompele et al. 2002), using GAPDH, B2M and β-actin (ACTB) as invariant controls. The following gene-specific primers, designed with Primer 0.5 software (Whitehead Institute for Biomedical Research), were used: Cathepsin K (for) 5'-CCC AGA CTC CAT CGA CTA TCG-3', (rev) 5'-CTG TAC CCT CTG CAC TTA GCT GCC-3'; TRAP (for) 5'-AAG ACT CAC TGG GTG GCT TTG-3', (rev) 5'-GGC AGT CAT GGG AGT TCA GG-3'; NFATc1 (for) 5'-GGT CTT CGG GAG AGG AGA AA-3', (rev) 5'-TGA CGT TGG AGG ATG CAT AG-3'; GAPDH (for) 5'-TGG GTG TGA ACC ATG AGA AGT ATG-3', (rev) 5'-GGT GCA GGA GGC ATT GCT-3'; B2M (for) 5'-TTC TGG CCT GGA GGC TAT C-3', (rev) 5'-TCA GGA AAT TTG ACT TTC CAT TC-3'; ACTB (for) 5'-CCA ACC GCG AGA AGA TGA-3', (rev) 5'-CCA GAG GCG TAC AGG GAT AG-3'. PCR conditions were as follows: 30 sec at 98° C. preincubation followed by 40 cycles of 15 sec at 95° C. and 30 sec at 60° C. (CathK, NFATc1, GAPDH, B2M, ACTB) or 30 sec at 60° C. followed by 30 sec at 79° C. (TRAP). Reaction products were characterized by determination of melting point (55-95° C. with 0.5° C./sec).

I.8 Western Blot Analysis

RAW264.7 cells were cultured in complete medium and starved for 2 hours prior to treatment with Pep8 (50 μM) in the presence or absence of RANKL (100 ng/mL). After treatment for 5, 10, 15, 30 or 60 minutes at 37° C., total cell lysates were obtained and protein concentrations were determined as described previously (Duplomb et al. 2008). For NF-κB pathway analysis, separate cytoplasmic and nuclear protein fractions were obtained using the NE-PER Nuclear and Cytoplasmic Extraction Kit (Thermo Scientific, UK). Proteins (40 μg) were run on 10% SDS—PAGE and transferred to Immobilon-P membranes (Millipore, Billerica, Mass., USA), which were then incubated with antibodies to Akt, phospho-Akt, ERK 1/2, phospho-ERK 1/2, p38, phospho-p38, IκBα, p105, p65, p50 and Rel B (Cell Signalling, Danvers, Mass., USA). The labeled proteins were detected using the ECL reagent (Pierce, Rockford, Ill., USA). β-Actin (total cell extract or cytoplasmic fraction), histone H3, and HDAC (nuclear fraction) were used as housekeeping proteins (Cell Signalling).

I.9 Cell Lines and Constructions

Murine RAW264.7 cells (ATCC) were cultured in αMEM (Invitrogen) supplemented with 10% FBS (Hyclone). Human embryonic kidney 293 cells (ATCC) were stably transduced with an expression-ready clone (Ex-00007-Lv105, Omics-Link™ Expression Clone, GeneCopoeia™) containing the ORF cDNA of RANK/TNFRSF11A. HEK-RANK cells were maintained in DMEM (Lonza), 10% FBS and 1 µg/mL puromycin.

I.10 Murine Model of Osteoporosis

Eight-week-old ovariectomized (OVX) female C57BL6 and non-ovariectomized control mice were purchased from Janvier (Le Genest Saint Ilsle, France). Mice were housed under pathogen-free conditions at the Experimental Therapy Unit (Faculty of Medicine, University of Nantes, France), and animal care and experimental protocols were approved by the French Ministry of Research and were done in accordance with the institutional guidelines of the French Ethical Committee and under the supervision of authorized investigators. After recovery from OVX surgery for 7 days and acclimation, the mice were randomly divided into treatment groups receiving daily subcutaneous injections of a peptide and a control group receiving daily injections of the vehicle (PBS) only. Non-ovariectomized or sham-operated mice were included in the studies as healthy controls. Three experimental protocols were established. Protocol 1: Ovariectomized mice received daily s.c. injections of 10 mg/kg body weight Pep8 (Pep8, n=8) or vehicle only (OVX, n=8). Non-ovariectomized (NOV, n=8) mice served as normal controls. Protocol 2: Ovariectomized mice were randomly divided into four groups (n=8), receiving daily treatments with pegylated Pep8 (Pep8-NPEG5) at 10 mg/kg or 2.5 mg/kg, or unpegylated Pep8 at a dose of 10 mg/kg/d, or the vehicle only. Sham-operated mice (n=5) served as healthy controls. Protocol 3: Ovariectomized mice receiving daily treatments with pegylated Pep8 (Pep8-NPEG8) at 10 mg/kg or 2.5 mg/kg, as described before, or unpegylated Pep8 at a lower dose of 2.5 mg/kg/d, or the vehicle only. Sham-operated mice (n=8) served as healthy controls.

During the experimental period, the body weight of the mice was monitored. No significant differences in the development of body weight were observed in ovariectomized mice during the course of the study. After treatment for five weeks, mice were anesthetized with isoflurane (2%, 1 L/min) and sacrificed by cervical dislocation. Lumbar vertebrae and tibiae were collected for micro-CT analysis and stored at 4° C. in 4% paraformaldehyde until further analysis. Additionally, internal organs (heart, liver, lungs, kidneys, spleen, intestines and thymus) of some mice (n=3 per group) were harvested and stored for toxicity screening.

I.11 Micro-CT Analysis of Bone Samples

Analysis of architectural variables of tibiae and vertebrae of mice was performed using the high-resolution X-ray micro-CT system for small animal imaging SkyScan-1072 (SkyScan, Belgium). After scanning, the image data were transferred to a workstation and the proximal tibiae and the fourth lumbar vertebrae (L4) were rendered for 3-D display and calculation of the structural indices (Parfitt et al. 1987) using the SkyScan analysis system (CT-analyser, CT-volume, SkyScan). For trabecular bone parameters in tibiae, transverse CT slices were obtained in the region of interest in the axial direction from the trabecular bone ca. 0.1 mm below the growth plate to the mid-femur. Contours were defined and drawn close to the cortical bone. The trabecular bone was then removed and analyzed separately. Fifty slices (1 mm) at approximately 0.4 µm distal to the growth plate of the proximal ends of the tibiae were used for analysis. For the analysis of the L4 vertebrae, 120 slices (2.4 mm) were manually delineated within the vertebral body to avoid the inclusion of the superior and inferior endplates. The threshold level for the measurements was set at 55 for the analyses. The analysis of the specimens involved the following bone measurements: bone volume fraction (BV/TV, %), trabecular number (TbN), trabecular thickness (TbTh) and trabecular spacing (TbSp).

I.12 Histological Evaluation of Organ Toxicity

After sacrifice, organs were conserved and fixed in 4% PFA at 4° C., and embedded in paraffin. Sections (4 µm) were cut and stained with hematoxylin and eosin (Lamoureux et al. 2009, Baud'Huin et al. 2010). General morphology of organs was evaluated on each section using a DMRXA microscope (Leica, Nussloch, Germany).

I.13 Statistical Analysis

In vivo data are presented as the mean±SEM of eight animals. The significance of differences between ovariectomized mice treated with the polypeptide and vehicle-treated animals or healthy controls was determined using ANOVA and Dunnett's multiple range test. For in vitro data, statistical analysis was performed by use of a 2-sided Student t test; comparisons between groups were analyzed by t test (2-sided) or ANOVA for experiments with more than 2 subgroups. Probability values of $P<0.05$ were considered statistically significant.

II. Results

II.1 RANKL Binding to RANK Allows to Define a Putative Inhibitory Region

One striking feature revealed in the structure of RANK-RANKL by the work of Liu et al. (2010) is the major conformational switch encompassed by RANK upon RANKL binding. Most of the bottom part of the extracellular region of RANK remains unchanged, the CRD1 and CRD2 units perform a 36° switch to come in close contact with RANKL (Liu et al. 2010). Although there is no strict cavity for defining a binding pocket, one can use the split resulting from the switch in the CRD2 domain to define the hinge region between the two conformations. The inventors used this cleft to define their main binding pocket for docking analysis of their polypeptide candidates (FIG. 1A).

II.2 Polypeptides of the Invention Targeting RANK Inhibit RANKL-Induced Osteoclastogenesis The inventors have designed several polypeptide inhibitors from the receptor RANK (Table 1) which were then screened for biological activity. The purified polypeptides (GeneCust) were prepared as 1 mM stock solutions in phosphate-buffered saline (PBS, pH 7.4) or cell medium. Due to the hydrophobic nature of some polypeptides, it was necessary to supplement the solvent with 1% DMSO to achieve the desired concentration. The inventors have evaluated these inhibitory polypeptides at a 50 µM concentration on osteoclastogenesis in human CD14$^+$ monocytes isolated from PBMCs cultured with 25 mg/mL M-CSF and 100 ng/mL RANKL (FIG. 1B). Polypeptide mimetics derived from OPG (OP3-4) and the TNF receptor (WP9QY) with a known inhibitory activity (Takasaki et al. 1997, Cheng et al. 2004), as well as the decoy receptor OPG at a concentration of 50 ng/mL were used as positive controls. Several of the designed polypeptides at a 50 µM concentration showed a moderate effect on osteoclast formation in vitro (Pep501 (SEQ ID NO: 24); PepA19 (SEQ ID NO: 29); PepA20 (SEQ ID NO: 30)), reducing the formation of TRAP-positive multinucleated cells by ca. 25-35% compared to cells treated with soluble RANKL alone.

Among the 8 new polypeptides screened in this assay, Pep8 (SEQ ID NO: 2) exhibited inhibitory activity similar to that of the RANKL-targeting mimetics OP3-4 and WP9QY, and was accordingly judged to be the most promising polypeptide inhibitor of RANK among the panel of polypeptides.

Figure 5:
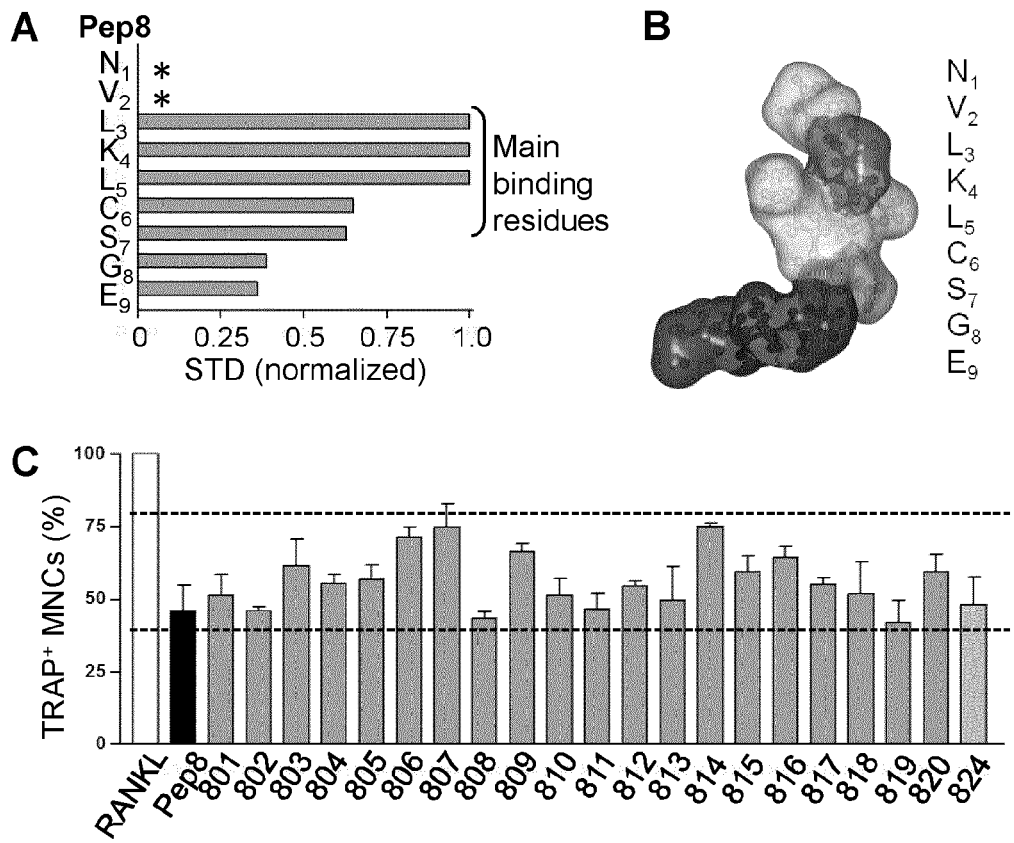
FIG. 5 (A-C) illustrates the characterization of the main binding residues and the inhibitory activity of a series of polypeptides of the invention on osteoclastogenesis. (A) Saturation transfer difference (STD) of Pep8 binding to RANK. The central motif Leu-Lys-Leu-Cys-Ser ($L_3K_4L_5C_6S_7$) receives the most important part of the transfer, which is in agreement with the predicted binding zone defined by molecular modeling. Due to experimental limitations, amino acids $N_1$ (Asp) and $V_2$ (Val) are not seen in the experiment. Both NH-groups from amino acid $N_1$ are detected, but show lower saturation transfers than NH from $G_8$ (Gly) and $E_9$ (Glu). (B) Three-dimensional conformation of Pep8 bound to RANK from molecular modeling. (C) Inhibitory activity of a series of polypeptides of the invention (series 800) on osteoclastogenesis. The polypeptides are derivatives of Pep8, which were generated based on molecular modeling results of specific binding affinities of key amino acids to RANK.

The inventors derived new polypeptides from the Pep8 sequence using molecular modeling as support for the modification. All these derived polypeptides were able to inhibit osteoclastogenesis in vitro and some of them had a stronger inhibition activity than Pep8 (FIG. 5C). All these derived polypeptides had a sequence comprising or consisting of a sequence selected from the group consisting of SEQ ID NO: 32 and a sequence having at least 80% of identity with SEQ ID NO: 32 over the entire length of SEQ ID NO: 32, SEQ ID NO: 33 and a sequence having at least 80% of identity with SEQ ID NO: 33 over the entire length of SEQ ID NO: 33, SEQ ID NO: 1 and a sequence having at least 80% of identity with SEQ ID NO: 1 over the entire length of SEQ ID NO: 1, in particular SEQ ID NO: 1 and a sequence having at least 80% of identity with SEQ ID NO: 1 over the entire length of SEQ ID NO: 1.

These results demonstrate the ability of the polypeptides according to the invention to inhibit RANKL-induced osteoclastogenesis in vitro.

TABLE 1

Polypeptides designed for binding to the RANK cleft. P8 series (Pep8 to Pep824) consisting of a sequence of up to 20 amino acids, wherein said sequence comprising or consisting of a sequence selected from the group consisting of SEQ ID NO: 32, SEQ ID NO: 33, SEQ ID NO: 1 and a sequence having at least 80% of identity with SEQ ID NO: 32, SEQ ID NO: 33 or SEQ ID NO: 1 over the entire length of SEQ ID NO: 32, SEQ ID NO: 33 or SEQ ID NO: 1, respectively.

| Name of the polypeptide | Amino acids sequence | Modifications* | % of identity with SEQ ID NO: 32, over the entire length of SEQ ID NO: 32, of a sequence comprised in the polypeptide | % of identity with SEQ ID NO: 33, over the entire length of SEQ ID NO: 33, of a sequence comprised in the polypeptide | % of identity with SEQ ID NO: 1, over the entire length of SEQ ID NO: 1, of a sequence comprised in the polypeptide | SEQ ID NO: |
|---|---|---|---|---|---|---|
| Pep822 | LKLCS | N-(PEG)$_5$/N-(PEG)$_8$ | 100% | 100% | 100% | 1 |
| Pep8 | NVLKLCSGE | N-(PEG)$_5$/N-(PEG)$_8$ | 100% | 100% | 100% | 2 |
| Pep801 | ELANVLKLCSGE | N-(PEG)$_5$/N-(PEG)$_8$ | 100% | 100% | 100% | 3 |
| Pep802 | NVLKLCSGEAY | N-(PEG)$_5$/N-(PEG)$_8$ | 100% | 100% | 100% | 4 |
| Pep803 | ELANVLKLCSGEAY | N-(PEG)$_5$/N-(PEG)$_8$ | 100% | 100% | 100% | 5 |
| Pep804 | NVLKLCSGEAYR | N-(PEG)$_5$/N-(PEG)$_8$ | 100% | 100% | 100% | 6 |
| Pep805 | NVLKLACSGE | N-(PEG)$_5$/N-(PEG)$_8$ | 83% | 83% | 83% | 7 |
| Pep806 | NVLKLCSE | N-(PEG)$_5$/N-(PEG)$_8$ | 100% | 100% | 100% | 8 |
| Pep808 | NVLKFCSGE | N-(PEG)$_5$/N-(PEG)$_8$ | 100% | 100% | 80% | 9 |
| Pep809 | NVIKLCSGE | N-(PEG)$_5$/N-(PEG)$_8$ | 80% | 80% | 80% | 10 |
| Pep810 | NVLKLCHGE | N-(PEG)$_5$/N-(PEG)$_8$ | 80% | 80% | 80% | 11 |
| Pep811 | ENVLKLCSGE | N-(PEG)$_5$/N-(PEG)$_8$ | 100% | 100% | 100% | 12 |
| Pep812 | NALKLCSGE | N-(PEG)$_5$/N-(PEG)$_8$ | 100% | 100% | 100% | 13 |
| Pep813 | EVLKLCSGN | N-(PEG)$_5$/N-(PEG)$_8$ | 100% | 100% | 100% | 14 |
| Pep814 | NALKLCSGEMR | N-(PEG)$_5$/N-(PEG)$_8$ | 100% | 100% | 100% | 15 |
| Pep815 | NALKLACSGE | N-(PEG)$_5$/N-(PEG)$_8$ | 83% | 83% | 83% | 16 |
| Pep816 | NALKLFCSGE | N-(PEG)$_5$/N-(PEG)$_8$ | 83% | 83% | 83% | 17 |
| Pep817 | NALRLCSGE | N-(PEG)$_5$/N-(PEG)$_8$ | 80% | 80% | 80% | 18 |
| Pep818 | NALHLCSGE | N-(PEG)$_5$/N-(PEG)$_8$ | 80% | 80% | 80% | 19 |
| Pep819 | NALFLCSGE | N-(PEG)$_5$/N-(PEG)$_8$ | 80% | 80% | 80% | 20 |
| Pep820 | NALNLCSGE | N-(PEG)$_5$/N-(PEG)$_8$ | 80% | 80% | 80% | 21 |
| Pep823 | YCNVLKLCSGECY | N-(PEG)$_5$/N-(PEG)$_8$ | 100% | 100% | 100% | 22 |
| Pep824 | NALKHCSGE | N-(PEG)$_5$/N-(PEG)$_8$ | 100% | 100% | 80% | 23 |
| Pep501 | ELASFLKISQLG | N-(PEG)$_5$/N-(PEG)$_8$ | X** | X** | X** | 24 |

TABLE 1-continued

Polypeptides designed for binding to the RANK cleft. P8 series (Pep8 to Pep824) consisting of a sequence of up to 20 amino acids, wherein said sequence comprising or consisting of a sequence selected from the group consisting of SEQ ID NO: 32, SEQ ID NO: 33, SEQ ID NO: 1 and a sequence having at least 80% of identity with SEQ ID NO: 32, SEQ ID NO: 33 or SEQ ID NO: 1 over the entire length of SEQ ID NO: 32, SEQ ID NO: 33 or SEQ ID NO: 1, respectively.

| Name of the polypeptide | Amino acids sequence | Modifications* | % of identity with SEQ ID NO: 32, over the entire length of SEQ ID NO: 32, of a sequence comprised in the polypeptide | % of identity with SEQ ID NO: 33, over the entire length of SEQ ID NO: 33, of a sequence comprised in the polypeptide | % of identity with SEQ ID NO: 1, over the entire length of SEQ ID NO: 1, of a sequence comprised in the polypeptide | SEQ ID NO: |
|---|---|---|---|---|---|---|
| Pep401 | ELASFNKITQLG | N-(PEG)$_5$/N-(PEG)$_8$ | X | X | X | 25 |
| Pep402 | ELASFNRITQLG | N-(PEG)$_5$/N-(PEG)$_8$ | X | X | X | 26 |
| PepA17 | WLETRLTNHMELQ | N-(PEG)$_5$/N-(PEG)$_8$ | X | X | X | 27 |
| PepA18 | AKFHGELMADQWQ | N-(PEG)$_5$/N-(PEG)$_8$ | X | X | X | 28 |
| PepA19 | NEMDLPKKSCLMN | N-(PEG)$_5$/N-(PEG)$_8$ | X | X | X | 29 |
| PepA20 | WAARLGDPT | N-(PEG)$_5$/N-(PEG)$_8$ | X | X | X | 30 |
| Pep1 | ELASYIIITQLG | N-(PEG)$_5$/N-(PEG)$_8$ | X | X | X | 31 |

*Modifications evaluated to improve the peptide stability and bioavailability.
**Data not calculated.

II.3 Kinetic Binding Ability of Inhibitory Polypeptides

Binding of the polypeptides to RANK was studied using surface plasmon resonance (FIG. 1C). Several polypeptides bound to immobilized RANK in a dose-dependent manner, presented here is Pep1 (SEQ ID NO: 33). Based on the association and dissociation kinetics obtained using a 1:1 Langmuir model for simple bimolecular interactions, the measured binding affinity ($K_d$) of Pep1 (FIG. 1C) to hRANK was 20.6 μM ($k_{on}$=1.35·10$^1$ M$^{-1}$s$^{-1}$, $k_{off}$=2.78·10$^{-4}$ s$^{-1}$). The polypeptide of the invention Pep8, bound RANK with a $K_d$ of 10.5 μM, and the apparent association constant ($k_{on}$) and disassociation constant ($k_{off}$) rate constants were estimated to be 4.95×10$^2$ M$^{-1}$s$^{-1}$ and 5.20×10$^{-3}$ s$^{-1}$ respectively.

These results demonstrate that the binding affinity ($K_d$) of the polypeptide of the invention, Pep8, to hRANK is greater than other tested polypeptides, such as Pep1.

II.4 Pep8 Inhibits RANKL-Induced Osteoclast Formation

The inhibitory activity of the polypeptide of the invention Pep8 was then examined more in detail on RANKL-induced osteoclast formation in human CD14$^+$ as well as murine CD11b$^+$ cells from C57/b16 mice. Mouse and human RANK show 77% amino acid sequence identity, therefore the inventors predicted that polypeptides generated on human RANK would also inhibit the mouse receptor homolog, and could therefore be tested in mouse models of bone loss.

Figure 2:
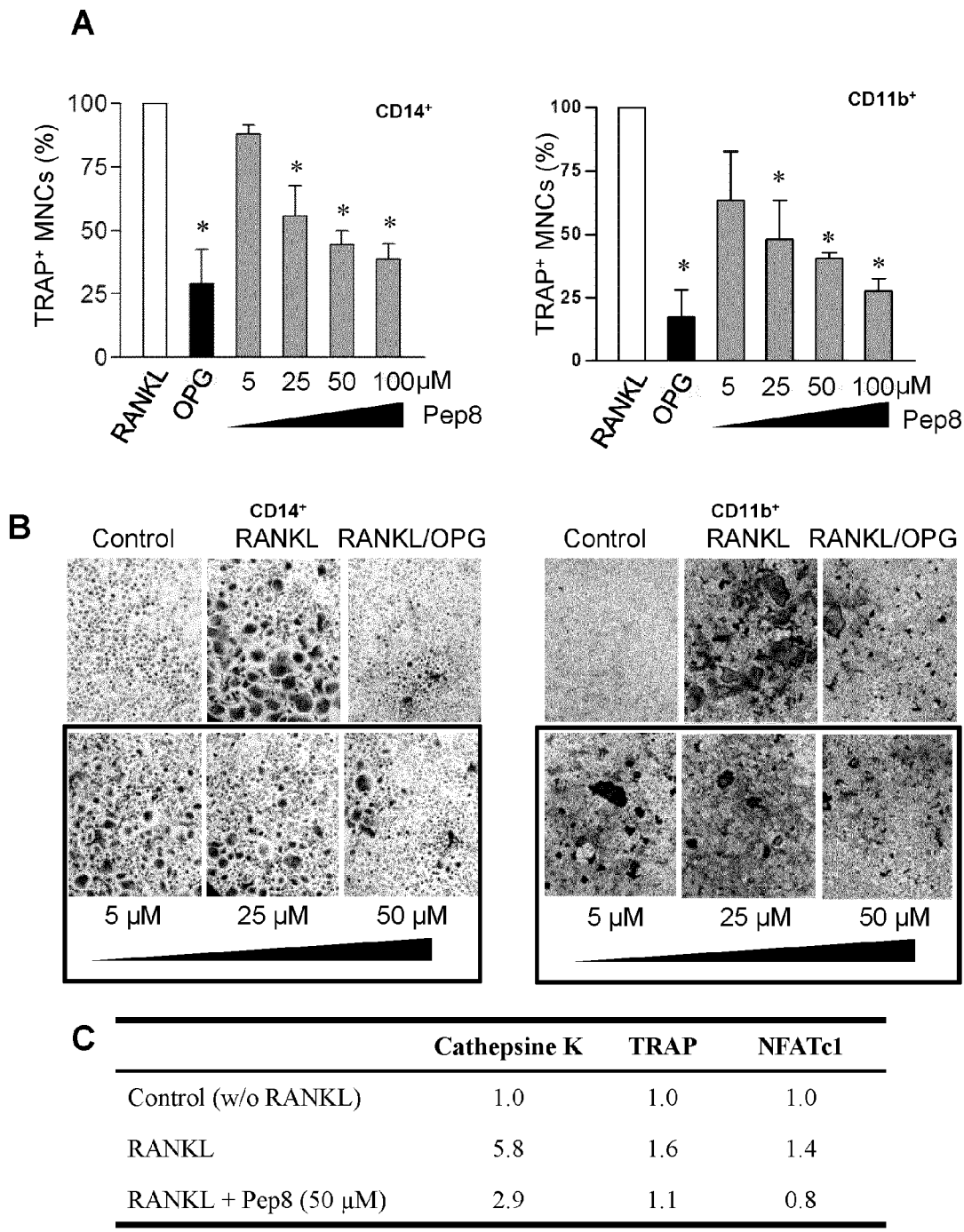
FIG. 2 (A-C) shows the inhibition of RANKL-induced osteoclastogenesis in vitro by Pep 8 (SEQ ID NO: 2). (A) Human monocytes were cultured with M-CSF and human RANKL in the presence or absence of increasing concentrations of Pep8, as indicated. OPG (50 ng/ml) was used as a reference inhibitor. Pep8 dose-dependently inhibited osteoclast formation in CD14$^+$ and CD11b$^+$ cells. Results are expressed as means±SD of at least two independent experiments carried out in triplicate versus treated with RANKL and M-SCF in the absence of Pep8 (RANKL). *P<0.05. (B) Representative microscopic images of TRAP$^+$ cells at different concentrations of Pep8. (C) Real-time quantitative RT-PCR analysis for relative expression of osteoclast-specific genes, cathepsin K, TRAP and nuclear factor of activated T cells c1 (NFATc1) showed that Pep8 inhibited the mRNA expression of cathepsin K, TRAP and NFATc1. CD14$^+$ cells were treated with M-SCF and sRANKL for 24 h in the presence or absence of Pep8 (50 Levels of the markers were normalized to beta-2-microglobulin (B2M). Expression level of undifferentiated cells (control) was set to 1. At least three independent experiments per marker were carried out. The table shows the results of a representative experiment.

Pep8 caused a dose-dependent decrease in the number of TRAP-positive multinucleated cells formed in human CD14$^+$ cells (FIG. 2A and B), as well as in murine cell cultures (data not shown). In the presence of 100 μM Pep8, the number of TRAP-positive multinucleated cells was 39% and 28% of the number formed in human or murine co-cultures, respectively, performed without the polypeptide. The IC$_{50}$ of Pep8 was 40 μM for human CD14$^+$ and 30 μM for murine CD11b$^+$ cells. Pep8 alone in the absence of RANKL did not modulate osteoclast development (data not shown).

Pep8 did not have intrinsic toxicity since there was no cytotoxic effect of 100 μM Pep8 on monocytes or murine macrophage-like RAW264.7 cells (data not shown), nor did the polypeptide at 100 μM exhibit any effect on mineralization of mesenchymal stem cells (MSCs), as evidenced by Alizarin red staining (data not shown).

Thus, these data suggest that Pep8 abrogates RANKL-induced osteoclastogenesis, without cytotoxicity.

To further elucidate the role of Pep8 on osteoclast differentiation, the inventors examined its effect on the gene expression of cathepsin K, TRAP, and nuclear factor of activated T cells c1 (NFATc1), all marker genes of osteoclasts. CD14$^+$ monocytes were treated with M-CSF (25 ng/mL) and hRANKL (100 ng/mL) in the absence or presence of Pep8 followed by total RNA isolation.

RT-PCR showed that the mRNA expression of osteogenic markers cathepsin K, TRAP and NFATc1 was markedly reduced in the presence of Pep8 at 3 days after RANKL stimulation, and this reduction of marker expression was maintained until day 11 (FIG. 2C), which is consistent with the inhibitory effect of Pep8 on osteoclastogenesis.

These results demonstrate the ability of the polypeptide of the invention Pep8 to inhibit the expression of marker genes of osteoclasts. Similar results were obtained with the pegylated Pep8 (Pep8-N(PEG)$_5$ and Pep8-N(PEG)$_8$).

II.5 Pep8 Inhibits RANKL-Induced Signaling

Figure 3:
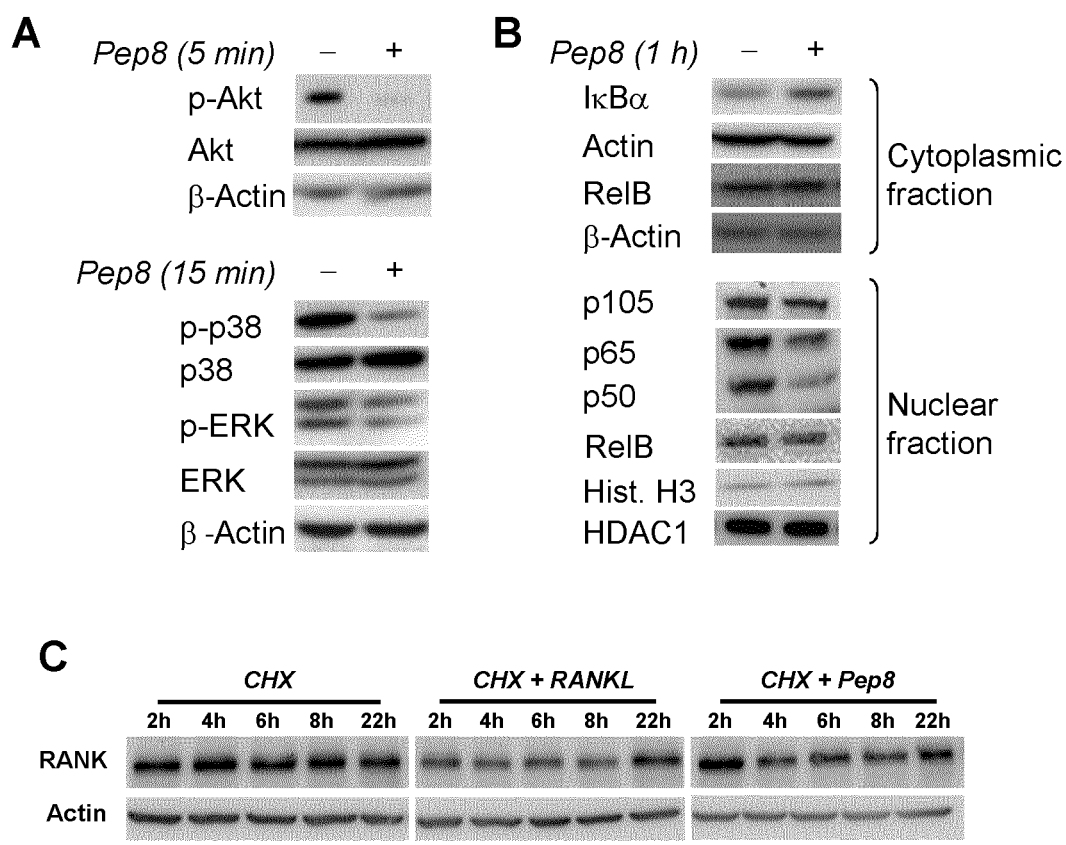
FIG. 3 (A-C) shows the inhibition of RANKL-induced signaling by Pep8. (A) Inhibition of activation of Akt, p38 and ERK by Pep8 (50 µM) was assessed as inhibition of phosphorylation (p) in RAW264.7 cells using Western blot analysis with antibodies against phospho-Akt, phospho-p38 and phospho-ERK. Immunoblots were stripped and then reprobed with antibodies against Akt, p38 and ERK. β-Actin served as loading control. (B) Western blot analyses of NF-κB distribution in the presence or absence of 50 µM Pep8. After treatment with the polypeptide, RAW264.7 cells were fractionated into nuclear and cytoplasmic portions. Nuclear proteins (45 µg) were analyzed with anti-NF-κB p105, p50 and p65 antibodies, while cytoplasmic proteins (30 µg) were analyzed with anti-IκBα. For the non-canonical NF-κB pathway, RelB expression was analyzed in both fractions. β-Actin, HDAC1 and Histone H3 served as loading controls for the cytoplasmic and nuclear fractions, respectively. A representative experiment is shown; time after RANKL stimulation is indicated in parenthesis. (C) Receptor half-life study. HEK-RANK cells were pre-incubated for 2 hours with 4 µg/mL cycloheximide (CHX), before treatment with RANKL (100 ng/mL) or Pep8 (200 µM) for the indicated times. RANK expression was determined with anti-RANK/TNFRSF11A.

To further explore pathways by which Pep8 regulates osteoclast differentiation and function, the effect of the polypeptide on RANKL-induced phosphorylation of Akt, p38 and ERK was examined in RAW264.7 cells that had been exposed to 50 μM Pep8. Western blot analyses demonstrated Akt phosphorylation after 5 minutes of RANKL treatment, and Pep8 exhibited an inhibitory effect on RANKL-induced Akt phosphorylation (FIG. 3A). Similarly, Pep8 inhibited phosphorylation of p38 and ERK after 15 minutes of RANKL treatment. The basal levels of pAkt and pERK were not changed in the presence of Pep8; however, Pep8 decreased phosphorylation of p38 even in the absence of RANKL stimulation (data not shown).

The inventors also examined whether Pep8 was capable of inhibiting the rapid RANKL-induced activation of NF-κB in RAW264.7 cells. The inventors found that the presence of Pep8 at 50 μM blocked the RANKL-induced degradation of IκBα and the subsequent nuclear translocation of p50 and p65 (FIG. 3B). These results indicate that Pep8 inhibits the RANKL-induced activation of the classical NF-κB pathway. By contrast, treatment with 50 μM Pep8 had no effect on the expression levels of RelB in the cytoplasmic as well as in the nuclear fraction (FIG. 3B).

The inventors confirmed the specificity of Pep8 on RANK signaling in human embryonic kidney cells overexpressing RANK. Pep8 strongly inhibited activation of p38 after stimulation with RANKL (FIG. 3C). In addition, RANKL treatment promoted the degradation of RANK over time in the presence of the protein synthesis inhibitor cycloheximide (CHX), while CHX alone did not. Similarly, treatment with CHX and Pep8 lead to a degradation of RANK, although to a somewhat lesser extent (FIG. 3C).

In conclusion, the polypeptide of the invention Pep8 seems to inhibit the RANKL-induced activation of the RANK signaling pathway.

II.6 Polypeptide Pep8 Protects Mice Against Ovariectomy-Associated Bone Loss

Given Pep8's ability to inhibit RANKL-induced osteoclast differentiation and signaling in vitro, the inventors asked whether Pep8 might prevent bone loss in vivo. Estrogen deficiency in ovariectomized mice leads to accelerated bone resorption and reduced bone mineral density (Sato et al. 1997). The inventors therefore examined whether Pep8 in vivo is able to protect against OVX-induced bone loss, which requires RANKL-signaling (Cenci et al. 2000, Roggia et al. 2001).

Figure 4:
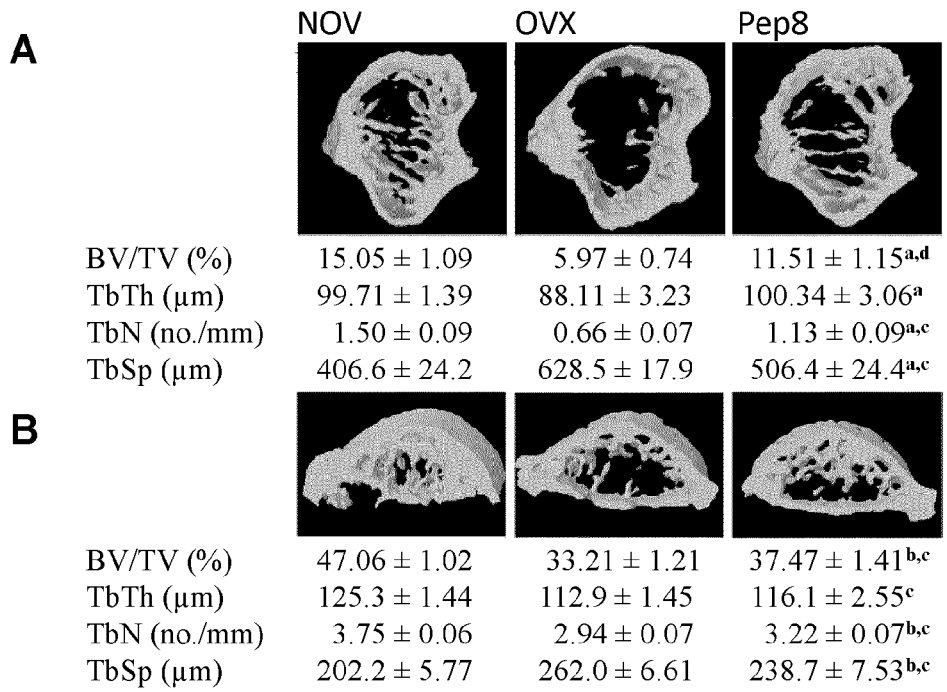
FIG. 4 (A-B) shows the inhibition of ovariectomy-induced bone loss by Pep8. The effect of Pep8 on in vivo bone density was determined in ovariectomized mice. 8-week-old C57BL/6 mice were ovariectomized and treated for 35 days with 10 mg/kg/day Pep8 or vehicle. Non-ovariectomized mice treated with the vehicle were included as healthy controls. The 3-dimensional structure of the trabecular bone in tibiae (A) and 4$^{th}$ lumbar vertebrae (B) was examined by micro-computed tomography (µCT), as described in Methods. The amount of trabecular bone in OVX mice was markedly less than the amount of trabecular bone in healthy controls (NOV). Treatment with Pep8 (10 mg/kg) prevented the loss of trabecular bone. Histomorphometric analysis shows a significant increase in bone volume (BV)/tissue volume (TV) ratio, trabecular thickness (TbTh), trabecular number (TbN), and decrease in trabecular spacing (TbS) in mice treated with Pep8. Values are the mean±SEM. $^a$P<0.005 and $^b$P<0.05 vs. OVX; $^c$P<0.005 and $^d$P<0.05 vs. NOV.

Female C57BL/6 mice underwent ovariectomy at 8 weeks of age and were allowed to recover from surgery for one week before treatment was initiated. Mice received daily subcutaneous injections of Pep8 for 35 days at a dosage of 10 mg/kg body weight daily. In vitro, Pep8 actively inhibited CD11b$^+$ osteoclast formation with an $IC_{50}$ of 30 μM (0.029 mg/mL). OVX control mice and age-matched healthy mice (NOV) were treated with the vehicle (PBS) only. Histomorphometry and μCT analysis demonstrated that treatment with Pep8 at a biologically active dose of 10 mg/kg/d induced an overall increase in trabecular bone density in ovariectomized mice compared with the vehicle-treated OVX control group (FIG. 4). The effectiveness of the OVX procedure was confirmed by a reduction of bone parameters such as the bone volume fraction (BV/TV), trabecular thickness (TbTh) and trabecular number (TbN), as well as an increase in trabecular spacing (TbS) in vehicle-treated OVX mice compared to healthy NOV mice (FIG. 4).

At the proximal tibia, treatment with Pep8 significantly increased trabecular BV/TV by 93% (P<0.01) in ovariectomized mice. TbTh increased by 14% (P<0.01) and TbN by 71% (P<0.01). Pep8-treated mice also exhibited a decline in TbS (P<0.01) compared with vehicle-treated mice (FIG. 4A).

Similar results were obtained in lumbar vertebrae (FIG. 4B). Vertebral trabecular BV/TV was lower in OVX than Pep8-treated mice (P<0.05). Similarly, treatment with Pep8 increased TbN (P<0.05) and reduced TbS (P<0.05). TbTh was also slightly, but not statistically significantly increased in mice treated with Pep8 compared to OVX control mice.

Figure 6:
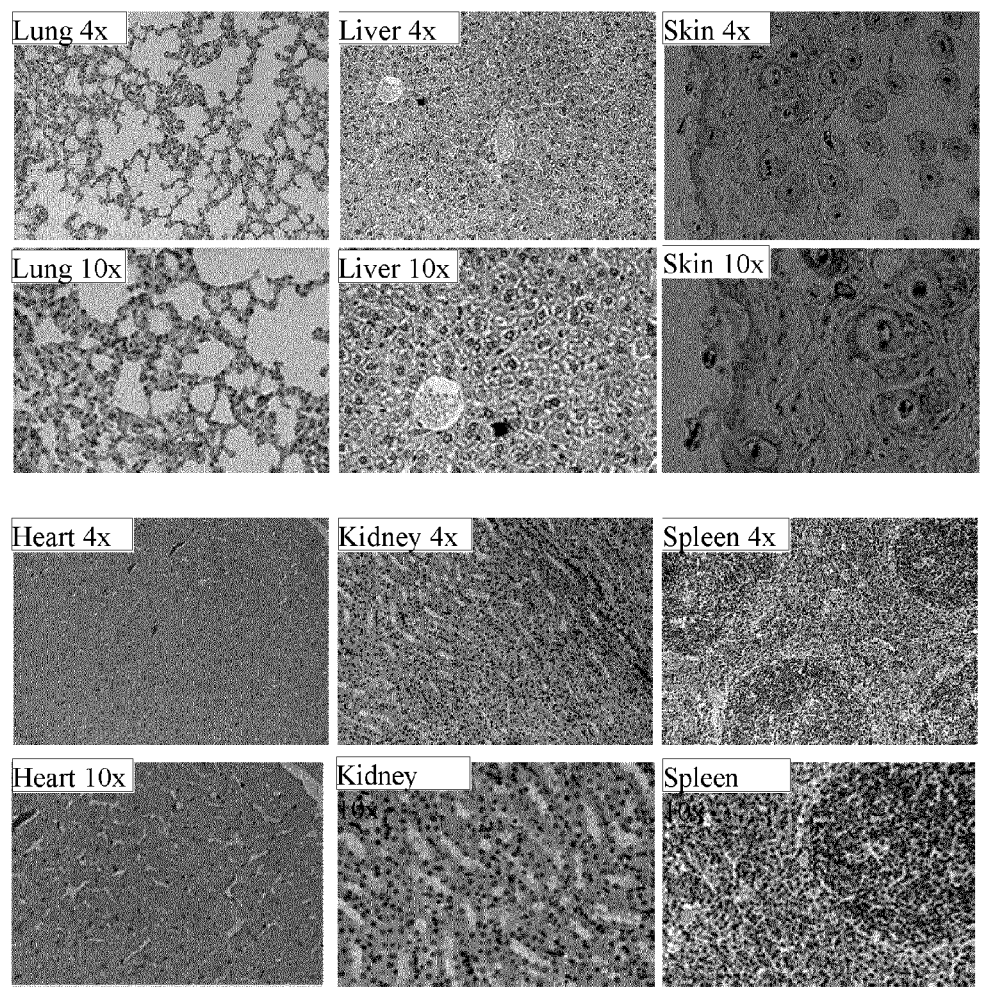
FIG. 6 represents the histomorphological evaluation of organ toxicity after treatment with Pep8 for 5 weeks. No histomorphological difference was observed compared to control groups.

Pep8 had no effect on the body weight in the OVX mice, indicating that a treatment at this dose had no toxic effects on animals, and this was confirmed by a histopathological evaluation of major organs (heart, lungs, liver, kidneys, spleen, skin) (FIG. 6).

Taken together, these results provide evidence that the polypeptide of the invention Pep8 can, at least partially, prevent postmenopausal bone loss in an in vivo animal model (by targeting RANK), without toxic effects.

A major concern for the use of therapeutic peptides remains their poor bioavailability due to rapid renal clearance (McGregor 2008). Although the peptide used in in vivo studies (Pep8) proved to be active at the concentration tested (10 mg/kg/day), the inventors asked whether peptide half-life could be further increased by N-terminal pegylation of the peptide. Peptide pegylation is well known to optimize peptide solubility, bioavailability and stability and decreases the immunogenicity. Pep8 carrying polyethylene glycol groups of two different chain lengths at the N-terminal amino acid (Pep8-N(PEG)$_5$ and Pep8-N(PEG)$_8$) were therefore tested in an ovariectomized mouse model, as described before.

Figure 7:
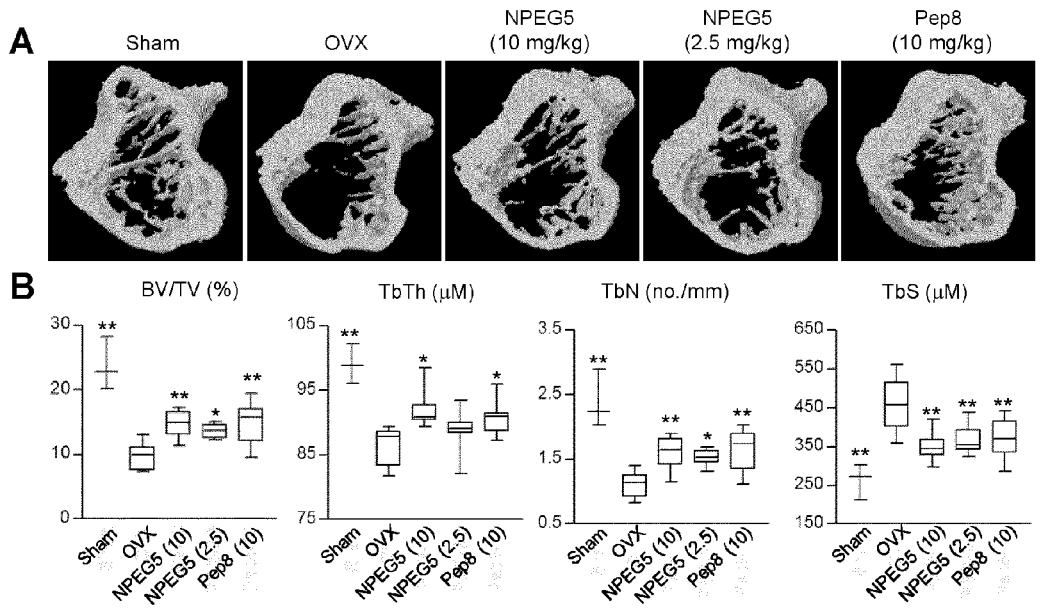
FIG. 7 (A-B) shows the inhibition of ovariectomy-induced bone loss by pegylated Pep8 (Pep8-NPEG5, NPEG5) compared to the unpegylated peptide. Ovariectomized C57BL/6 mice were treated with daily doses of 10 mg/kg or 2.5 mg/kg Pep8-NPEG5 or with 10 mg/kg unpegylated Pep8 for 35 days and bone density was evaluated as described before. (A) Representative three-dimensional transversal µCT Images of the proximal region of tibiae from mice treated with Pep8-NPEG5 (10 mg/kg/d, n=8 or 2.5 mg/kg/d, n=8), Pep8 (10 mg/kg/d, n=7), or vehicle (OVX, n=8). Sham-operated mice (n=5) served as healthy controls. (B) Histomorphometric analysis of tibiae shows a significant increase in bone volume/tissue volume (BV/TV) ratio, trabecular thickness (TbTh) and trabecular number (TbN), as well as a decrease in trabecular spacing (TbS) in mice treated with Pep8-NPEG5 or unpegylated Pep8 at a dose of 10 mg/kg compared to vehicle-treated mice. Treatment of mice with Pep8-NPEG5 at a lower dose (2.5 mg/kg) was almost as effective, significantly increasing BV/TV and TbN, as well as decreasing TbS in tibiae. Values are the mean±SEM; **, P<0.01; *, P<0.05.

Mice received daily subcutaneous injections of Pep8-NPEG5 at two different doses, 10 mg/kg and 2.5 mg/kg body weight. Unpegylated Pep8 at 10 mg/kg served as positive control. OVX control mice and sham-operated mice (Sham) were treated with the vehicle (PBS) only. μCT analysis of the tibiae showed that treatment with Pep8-NPEG5 at a dose of 10 mg/kg/d attenuated bone loss in OVX mice to the same extent as treatment with the unpegylated peptide (FIG. 7), as demonstrated by a significant increase in structural parameters, including trabecular BV/TV, TbTh, and TbN with an decrease in TbS. However, Pep8-NPEG5 at a 4-fold lower dose of 2.5 mg/kg/d was almost as effective as both, the pegylated and the unpegylated Pep8 at 10 mg/kg/d, significantly increasing BV/TV and TbN and decreasing TbS in the proximal tibiae (FIG. 7).

Figure 8:
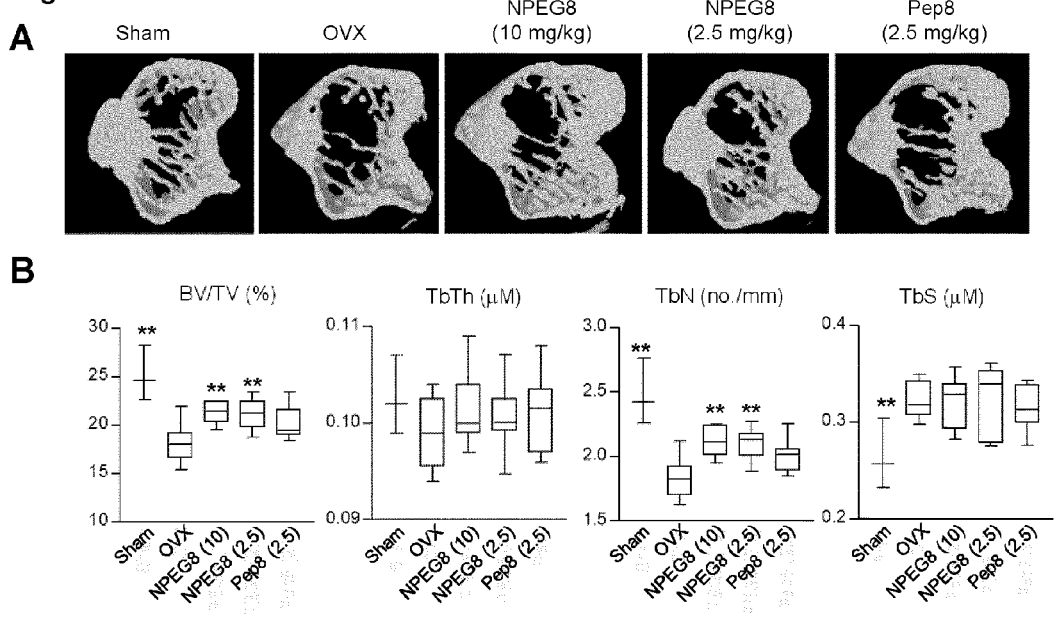
FIG. 8 (A-B) shows the inhibition of ovariectomy-induced bone loss by pegylated Pep8 (Pep8-NPEG8, NPEG8) compared to the unpegylated peptide. Ovariectomized C57BL/6 mice were treated with daily doses of 10 mg/kg or 2.5 mg/kg Pep8-NPEG8 or with unpegylated Pep8 at a lower dose of 2.5 mg/kg for 35 days and bone density was evaluated as described before. (A) Representative three-dimensional transversal µCT Images of the proximal region of tibiae from mice treated with Pep8-NPEG8 (10 mg/kg/d, n=8 or 2.5 mg/kg/d, n=8), Pep8 (2.5 mg/kg/d, n=8), or vehicle (OVX, n=8) Sham-operated mice (n=8) served as healthy controls. (B) Histomorphometric analysis of tibiae show a significant increase in bone volume/tissue volume (BV/TV) ratio and trabecular thickness (TbTh) for Pep8-NPEG8 treated groups at both dosages compared to vehicle-treated mice, while Pep8 at a lower dose of 2.5 mg/kg was less efficient. Values are the mean±SEM **, P<0.01.
Figure 9:
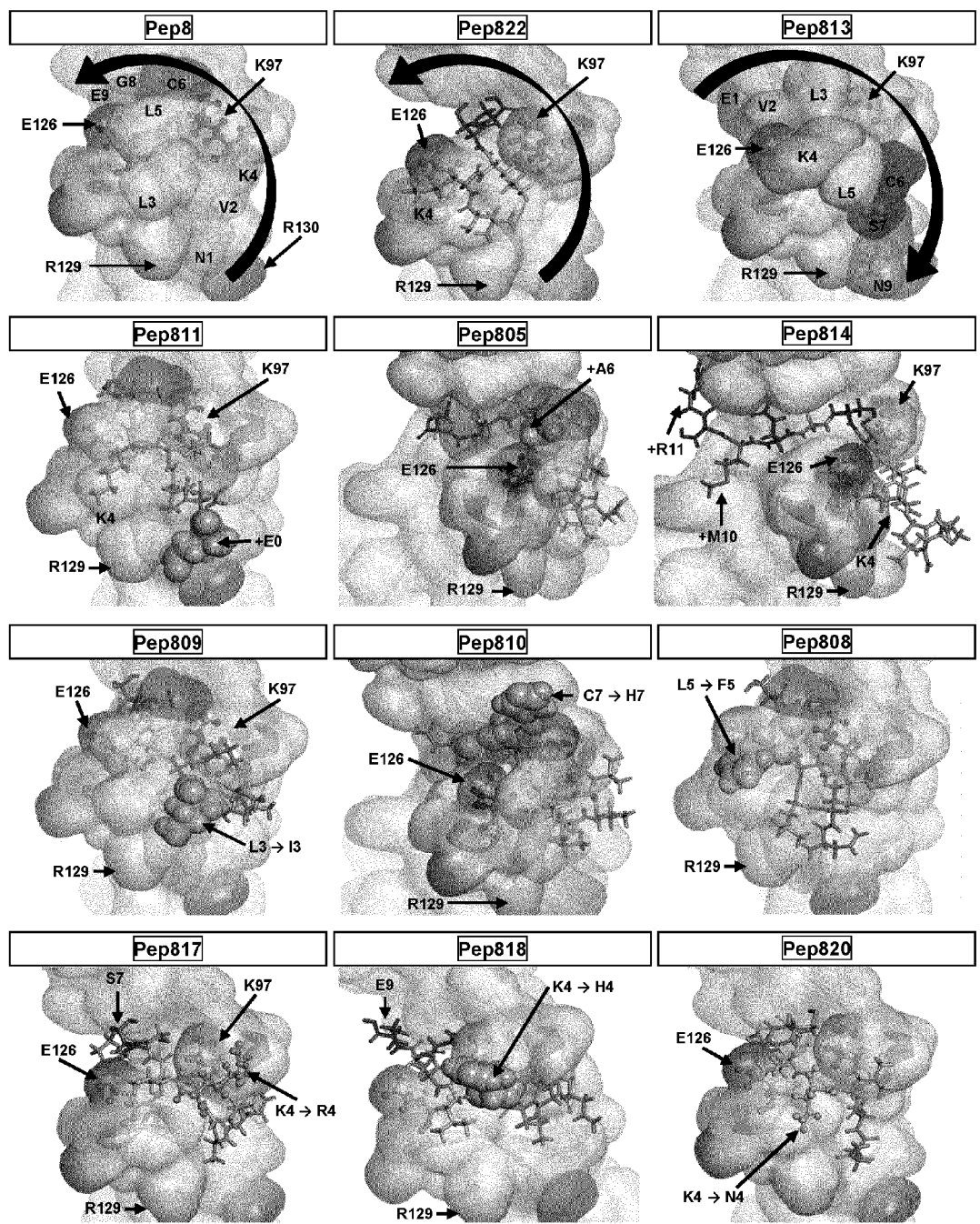
FIG. 9 shows representative docking results of Pep8 derivatives bound to RANK. RANK is displayed as a soft volume colored according to interpolated amino acid charges (in the original figure: red: negative, blue: positive, white: neutral). In the original figure amino acid substitutions are in yellow and rendered using the CPK representation. In the original figure: E126 is red, R129 and K97 are blue, V2 and N9 are orange, L3 is light green, K4 is green, L5 is light blue, E1 is pink, S7 is light violet and C6 is violet. Top row: Pep8 orientation and sequence is presented for reference with volumes colored according to amino acids in the original figure; the main amino acids of RANK defining the binding crevice are indicated by arrows. Big arrow represents the peptide orientation on RANK. Amino acid K4 is positioned towards RANK-E$_{126}$ instead of adopting the head-to-tail orientation with RANK-$K_{97}$ when only the core motif $L_3$-$K_4$-$L_5$-$C_6$—$S_7$ is present (Pep822). The peptide orientation is reversed if amino acids in position 1 and 9 are exchanged (Pep813). Second row: if the peptide length is increased in N-terminal (Pep811) or C-terminal (Pep814, Pep805) position, the resulting peptide adopts a more stretched conformation, displacing K4 from its optimal position. Third row: modifying the conformational state of $L_3$ (Pep809) or increasing the positional lock of $C_7$ or $L_5$ (Pep810 and 808) results in a displacement of the N-terminal end of the peptide. The additional decrease in C-terminal peptide entropy induced by these changes is counter-balanced by the loss of binding at the N-terminal end, although the $K_4$ orientation is kept. Bottom row: the substitution of $K_4$ can be compensated by alternative binding patterns where amino acid positions are shifted (Pep817), by disrupting $R_{129}/R_{130}$-binding by $N_1$ (Pep818), or alternative binding conformations (Pep820) similar to that observed with Pep822.
Figure 10:
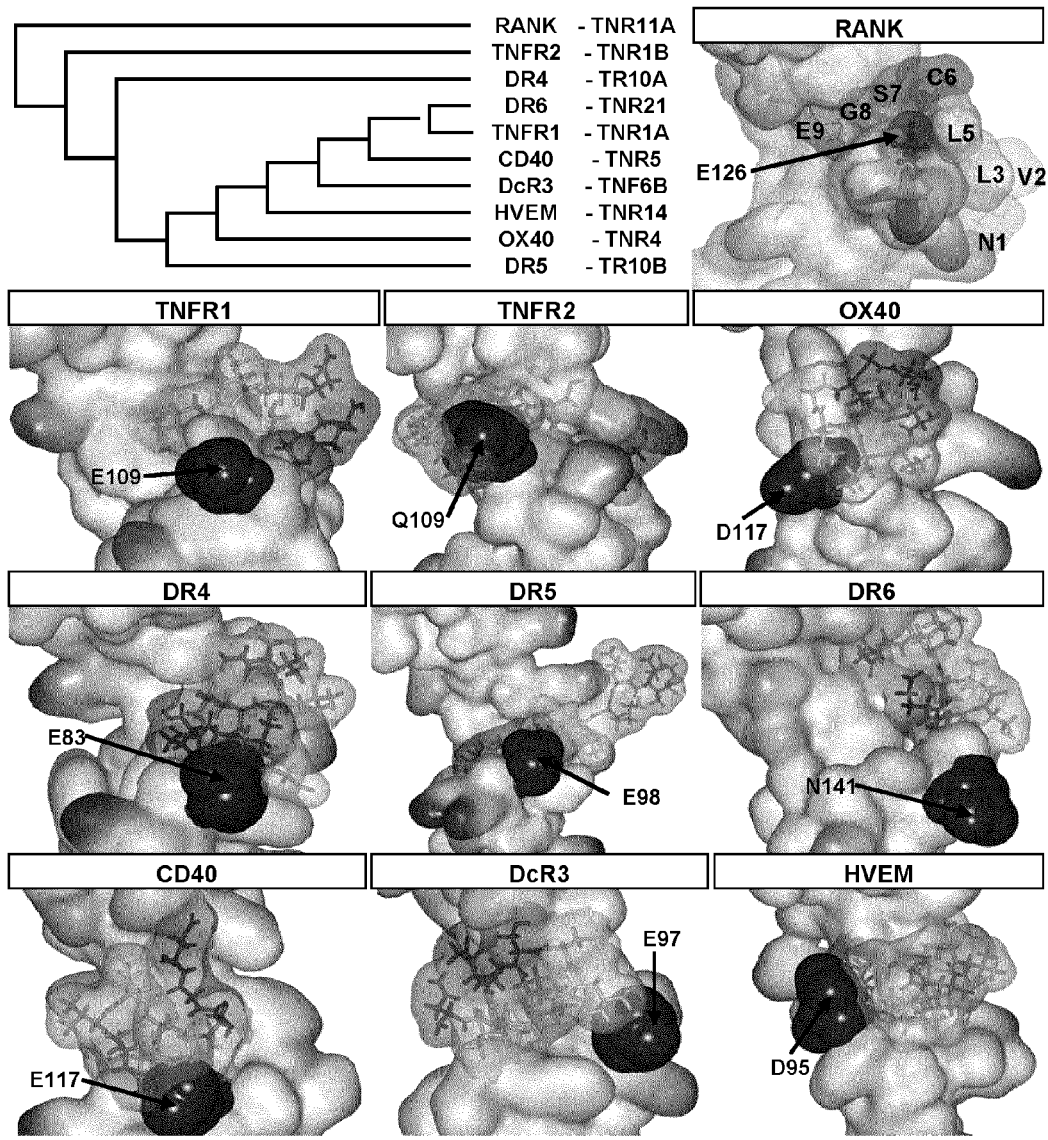
FIG. 10 shows the docking results of Pep8 on various TNF-R members. A phylogenetic tree produced with Seaview (Galtier et al. 1996) shows the relative proximity of RANK with other members of the TNF-R family (top left). Images of TNF-R members from experimental structures (Liu et al. 2010; Banner et al. 1993; Mukai et al. 2010; Compaan et al. 2005; Zhan et al. 2011; Cha et al. 2000; Kuester et al. 2011; An et al. 2011; Compaan et al. 2006)) and the DR4 model structure (name in grey) derived from the DR5 crystallographic structure (Picarda et al. 2012) in complex with Pep8 are shown. In the original figure: E9, G8 and S7 are light violet, C6 is violet, L5 is light blue, L3 is light green, V2 is orange, E126 of RANK, E109 of TNFR1, Q109 of TNFR2, D117 of OX40, E83 of DR4, E98 of DR5, N141 of DR6, E117 of CD40, E97 of DcR3 and D95 of HVEM are red. Unlike for RANK, no extended binding cavity could be defined on other TNF-R members. The amino acid equivalent to RANK-$E_{126}$ (CPK representation in red in the original figure: E109 of TNFR1, Q109 of TNFR2, D117 of OX40, E83 of DR4, E98 of DR5, N141 of DR6, E117 of CD40, E97 of DcR3 and D95 of HVEM) was identified manually from the crystal structure of the corresponding TNF receptor/ligand complex. DR6 has no bound ligand and displays an open conformation, with no potential binding groove for the peptide. Docking experiments suggested that no Pep8 conformation is able to wrap properly around the targeted amino acid to block ligand binding. Only some Pep8 residues are able to nonspecifically bind to a receptor. The core motif $L_3$-$K_4$-$L_5$-$C_6$—$S_7$, responsible for RANK-specificity, is often exposed to the solvent or involved in internal peptide interactions rather than interactions with the protein.

In a second experiment, ovariectomized mice were randomized into different treatment groups receiving daily treatments with Pep8-NPEG8 at 2.5 or 10 mg/kg, or unpegylated Pep8 at a lower dose of 2.5 mg/kg body weight. As expected, Pep8-NPEG8 showed similar activity at both tested doses, significantly increasing trabecular BV/TV and TbN compared to vehicle-treated animals (FIG. 8). By contrast, Pep8 at the lower dose of 2.5 mg/kg was less efficient, only slightly, but not significantly increasing BV/TV and TbN, indicating a dose-dependent effect of the peptide.

Taken together, these results indicate that pegylation increases the bioavailability of the peptide, thereby allowing a significant reduction of the dose while achieving the same protective effect on bone loss.

II.7 STD NMR Study of the Interaction Between Pep8 RANK

A Saturation Transfer Difference (STD-NMR) experiment was performed with hRANK and Pep8 in a phosphate buffer (FIG. 5A). Pep8 spectra were measured first without the protein, and the polypeptide remained stable under the experimental NMR conditions throughout the length of the experiment (2 weeks). hRANK was also studied in the same phosphate buffer, and increasing concentrations of Pep8 (with a concentration ratio from 100:1 to 1000:1) were added to the NMR tube to analyze the Pep8-hRANK interaction. The spectra of Pep8 bound to RANK differed significantly from that of the soluble unbound Pep8, in a dose-dependent manner, proportional to the addition of Pep8 to the NMR tube. The Pep8/hRANK interaction was analyzed more than two weeks after adding the polypeptide to the mix, and no additional visible shifts in the bound spectra were observed, apart from those induced by the binding of Pep8 to its target RANK. The STD experiment revealed that the 5 central amino acids of Pep8 were in direct interaction with hRANK ($L_3K_4L_5C_6S_7$) with three receiving 100% of the saturation ($L_3K_4L_5$). $C_6S_7$ had a relative transfer ratio of 60% and $G_8E_9$ received lower transfers. $N_1V_2$ were not visible in the spectra, which is typical in this type of experiment, but both terminal NH of $N_1$ were detectable with a signal close to the signal of $G_8E_9$. These results indicate that Pep8 forms a tight interaction with hRANK and that most of these interactions are concentrated in the core 5 amino acids ($L_3K_4L_5C_6S_7$, at least for the backbone NH). These interactions define a continuous patch of interactions throughout hRANK, which is in perfect agreement with the positions inferred from the molecular modeling analysis (FIGS. 1A and 5B).

These results provide clear evidences of the direct interaction of the polypeptide of the invention Pep8 with hRANK, in a conformation which is in agreement with the modeled interaction.

BIBLIOGRAPHIC REFERENCES

An H-J et al. (2011) Crystallographic and mutational analysis of the CD40-CD154 complex and its implications for receptor activation. J Biol Chem. 286(13):11226-11235.

Aoki K, Saito H, Itzstein C, et al. (2006). A TNF receptor loop peptide mimic blocks RANK ligand-induced signaling, bone resorption, and bone loss. J Clin Invest 116: 1525-1534.

Banner D W et al. (1993) Crystal structure of the soluble human 55 kd TNF receptor-human TNF beta complex: implications for TNF receptor activation. Cell. 73(3):431-45. Baron R, Ferrari S, and Russell R. (2011). Denosumab and bisphosphonates: Different mechanisms of action and effects. Bone 48: 677-692.

Baud'Huin M, Duplomb L, Téletchéa S, et at (2009). Factor VIII-von Willebrand factor complex inhibits osteoclastogenesis and controls cell survival J Biol Chem 284: 31704-13.

Baud'Huin M, Renault R, Charrier C, et at (2010). Interleukin-34 is expressed by giant cell tumours of bone and plays a key role in RANKL-induced osteoclastogenesis. J Pathol 221 (1): 77-86.

Bax A and Davis D G (1985). MLEV-17-based two-dimensional homonuclear magnetization transfer spectroscopy, J Magn Reson 65: 355-60.

Boyce B F, Xing L, Yao Z, et al. (2006). Future Anti-Catabolic Therapeutic Targets in Bone Disease. Annals of the New York Academy of Sciences 1068: 447-457.

Brooks B R, Bruccoleri R E, Olafson B D, et at (1983). CHARMM: A Program for Macromolecular Energy, Minimization, and Dynamics Calculations, J Comp Chem 4: 187-217.

Cenci S, Weitzmann M N, Roggia C, et at (2000). Estrogen deficiency induces bone loss by enhancing T-cell production of TNF-α. J Clin Invest 106: 1229-37.

Cha S-S et al. (2000) Crystal structure of TRAIL-DR5 complex identifies a critical role of the unique frame insertion in conferring recognition specificity. J Biol Chem. 275 (40):31171-31177.

Cheng X, Kinosaki M, Takami M, et at (2004). Disabling of Receptor Activator of Nuclear Factor-kB (RANK) Receptor Complex by Novel Osteoprotegerin-like Peptidomimetics Restores Bone Loss in Vivo. J Biol Chem 279 (9): 8269-77. Compaan D M, Gonzalez L C, Tom I, Loyet K M, Eaton D, and Hymowitz S G. (2005) Attenuating lymphocyte activity: the crystal structure of the TLA-HVEM complex. J Biol Chem. 280(47):39553-39561.

Compaan D M, and Hymowitz S G. (2006) The crystal structure of the costimulatory OX40-OX40L complex. Structure. 14(8):1321-1330.

Cutting B, Shelke S V, Dragic Z, et at (2007). Sensitivity enhancement in saturation transfer difference (STD) experiments through optimized excitation schemes. Magn Reson Chem 45 (9): 720-24.

Dai X, Ma W, He X, et al. (2011). Review of therapeutic strategies for osteosarcoma, chondrosarcoma, and Ewing's sarcoma. Med. Sci. Monit. 17: RA177-RA190.

Demchenko Y N, and Kuehl W M. (2010). A critical role for the NFkB pathway in multiple myeloma. Oncotarget 1: 59-68.

Derossi D, Joliot A H, Chassaing G, and Prochiantz A. (1994). The third helix of the Antennapedia homeodomain translocates through biological membranes. Journal of Biological Chemistry 269: 10444-10450.

Duplomb L, Baud'huin M, Charrier C, et al. (2008). Interleukin-6 inhibits receptor activator of nuclear factor-κB ligand-induced osteoclastogenesis by diverting cells into the macrophage lineage: key role of Serine727 phosphorylation of signal transducer and activator of transcription 3. Endocrinology 149: 3688-97.

Duheron V, Hess E, Duval M, et al. (2011). Receptor activator of NF-κB (RANK) stimulates the proliferation of epithelial cells of the epidermo-pilosebaceous unit. PNAS 108: 5342-5347.

Galtier N, Gouy M, and Gautier C. (1996) SEAVIEW and PHYLO WIN: two graphic tools for sequence alignment and molecular phylogeny. Comput Appl Biosci. 12(6):543-548.

Gonzalez-Suarez E, Jacob A P, Jones J, et al. (2010). RANK ligand mediates progestin-induced mammary epithelial proliferation and carcinogenesis. Nature 468: 103-107.

Hansen K E, Wilson H A, Zapalowski C, et al. (2011). Uncertainties in the prevention and treatment of glucocorticoid-induced osteoporosis. Journal of Bone and Mineral Research 26: 1989-1996.

Hwang T L and Shaka A J (1995). Water Suppression That Works—Excitation Sculpting Using Arbitrary Wave-Forms and Pulsed-Field Gradients, J Magn Reson Ser A 112: 275-79.

Kuester M, Kemmerzehl S, Dahms S O, Roeser D, and Than M E. (2011) The crystal structure of Death Receptor 6 (DR6): a potential receptor of the Amyloid Precursor Protein (APP). J Mol Biol. 409(2):189-201.

Lamoureux F, Picarda G, Garrigue L, et at (2009). Glycosaminoglycans as potential regulators of osteoprotegerin therapeutic activity in osteosarcoma. Cancer Res 69: 526-36.

Jones D H, Nakashima T, Sanchez O H, et al. (2006). Regulation of cancer cell migration and bone metastasis by RANKL. Nature 440: 692-696.

Lee B L, Higgins M J, and Goss P E. (2011). Denosumab and the current status of bone-modifying drugs in breast cancer. Acta Oncologica, 1-11.

Lien S, and Lowman H B. (2003). Therapeutic peptides. Trends in Biotechnology 21: 556-562.

Liu C, Walter T S, Huang P, et at (2010). Structural and Functional Insights of RANKL-RANK Interaction and Signaling. J Immunol 184: 6910-19.

McGregor D P (2008) Discovering and improving novel peptide therapeutics. Current Opinion in Pharmacology 8:616-619.

May M J, D'Acquisto F, Madge L A, et al. (2000). Selective Inhibition of NF-κB Activation by a Peptide That Blocks the Interaction of NEMO with the IκB Kinase Complex. Science 289: 1550-1554.

Mori K, Berreur M, Blanchard F, et al. (2007). Receptor activator of nuclear factor-kappaB ligand (RANKL) directly modulates the gene expression profile of RANK-positive Saos-2 human osteosarcoma cells. Oncol Rep 18: 1365-1371.

Mukai Y et al. (2010) Solution of the structure of the TNF-TNFR2 complex. Sci Signal. 3(148):ra83.

Needleman S B, and Wunsch C D. (1970). A general method applicable to the search for similarities in the amino acid sequence of two proteins. Journal of Molecular Biology 48: 443-453.

Parfitt A M, Drezner M K, Glorieux F H, et al. (1997). Bone histomorphometry: standardization of nomenclature, symbols, and units. Report of the ASBMR Histomorphometry Nomenclature Committee. J Bone Miner Res 2 (6): 595-610.

Petersen T N, Brunak S, von Heijne G, et al. (2011). SignalP 4.0: discriminating signal peptides from transmembrane regions. Nat Meth 8: 785-786.

Picarda G et al. (2012) A functional, new short isoform of Death Receptor 4 in Ewing's sarcoma cell lines may be involved in TRAIL sensitivity/resistance mechanisms. Mol Cancer Res. 10(3):336-346.

Piotto M, Saudek V and Sklenar V (1992). Gradient-tailored excitation for single-quantum NMR spectroscopy of aqueous solutions. J Biomol NMR 2 (6): 661-65.

Pons J, Tanchou V, Girault J P, Bertho G, Evrard-Todeschi N (2011). NMR applications for identifying β-TrCP protein-ligand interactions. Med Chem 11 (4): 283-97. Review.

Roggia C, et al. (2001). Up-regulation of TNF-producing T cells in the bone marrow: a key mechanism by which estrogen deficiency induces bone loss in vivo. Proc Natl Acad Sci USA 98: 13960-65.

Sato M, Zeng G Q and Turner C H (1997). Biosynthetic human parathyroid hormone (1-34) effects on bone quality in aged ovariectomized rats. Endocrinology 138: 4330-4337.

Santini D, Perrone G, Roato I, et al. (2011). Expression pattern of receptor activator of NFκB (RANK) in a series of primary solid tumors and related bone metastases. Journal of Cellular Physiology 226: 780-784.

Schramek D, Leibbrandt A, Sigl V, et al. (2010). Osteoclast differentiation factor RANKL controls development of progestin-driven mammary cancer. Nature 468: 98-102.

Smith H S. (2011). Painful osseous metastases. Pain Physician 14: E373E403.

States D J, Haberkorn R A, Ruben D J (1982). A two-dimensional nuclear Overhauser experiment with pure absorption phase in four quadrants. J Magn Res 48: 286-92.

Ta H M, Nguyena G T T, Jinb H M, et at (2010). Structure-based development of a receptor activator of nuclear factor-KB ligand (RANKL) inhibitor peptide and molecular basis for osteopetrosis. PNAS 107 (47): 20281-86.

Takasaki W, Kajino Y, Kajino K, et at (1997). Structure-based design and characterization of exocyclic peptidomimetics that inhibit TNFα binding to its receptor. Nat Biotech 15: 1266-70.

Tanaka S, Nakamura K, Takahasi N, et al. (2005). Role of RANKL in physiological and pathological bone resorption and therapeutics targeting the RANKL—RANK signaling system. Immunological Reviews 208: 30-49.

Theoleyre S, Wittrant Y, Tat S K, et al. (2004). The molecular triad OPG/RANK/RANKL: involvement in the orchestration of pathophysiological bone remodeling. Cytokine Growth Factor Rev 15: 457-475.

Toes R E M, van der Voort E I H, Schoenberger S P, et al. (1998). Enhancement of Tumor Outgrowth Through CTL Tolerization After Peptide Vaccination Is Avoided by Peptide Presentation on Dendritic Cells. The Journal of Immunology 160: 4449-4456.

Vandesompele J, De Preter K, Pattyn F, et al. (2002). Accurate normalization of real-time quantitative RT-PCR data by geometric averaging of multiple internal control genes. Genome Biol 3: RESEARCH0034.

Whyte L S, Ryberg E, Sims N A, et al. (2009). The putative cannabinoid receptor GPR55 affects osteoclast function in vitro and bone mass in vivo. PNAS 106: 16511-16516.

Wittig J C, Bickels J, Priebat D, et al. (2002). Osteosarcoma: a multidisciplinary approach to diagnosis and treatment. Am Fam Physician 65: 1123-1132.

Wu G, Robertson D H, Brooks C L, et at (2003). Detailed analysis of grid-based molecular docking: A case study of CDOCKER-A CHARMm-based MD docking algorithm. J Comp Chem 24 (13): 1549-62.

Xia Y, Zhu Q, Jun K Y, Wang J, Gao X (2010). Clean STD-NMR spectrum for improved detection of ligand-protein interactions at low concentration of protein. Magn Reson Chem 48 (12): 918-24.

Xu M, Choudhary S, Voznesensky 0, et at (2010). Basal bone phenotype and increased anabolic responses to intermittent parathyroid hormone in healthy male COX-2 knockout mice. Bone 47: 341-352.

Zhan C et al. (2011) Decoy strategies: the structure of TL1A: DcR3 complex. Structure. 19(2):162-171.

The invention claimed is:

1. A method of treating a bone resorptive disease selected from the group consisting of osteoporosis, osteolytic bone disease, primary bone cancers, secondary bone cancers, periodontal disease, and rheumatoid arthritis, comprising administering to a patient in need thereof an isolated polypeptide consisting of a sequence of up to 14 amino acids, wherein said sequence comprises a sequence selected from the group consisting of:
   (a) SEQ ID NO:1; and
   (b) a sequence having at least 80% of identity with SEQ ID NO:1 after global alignment over the entire length of the sequence with SEQ ID NO:1.

2. The method of claim 1, wherein said polypeptide comprises a sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, and SEQ ID NO:23.

3. The method of claim 1, wherein said polypeptide consists of the sequence of SEQ ID NO: 1.

4. The method of claim 2, wherein said polypeptide consists of the sequence of SEQ ID NO: 2.

5. The method of claim 1, wherein said polypeptide contains at least one biochemical modification selected from the group consisting of pegylation, acetylation, formylation, myristic acid addition, palmytoylation, benzyloxycarbonylation, amidation, succinylation, and glycosylation.

6. The method of claim 1, further comprising administering another bone anti-resorptive agent.

7. The method according to claim 6, wherein said another bone anti-resorptive agent is selected from the group consisting of:
   (a) an anabolism enhancer selected from the group consisting of parathyroid hormone, bone morphogenic protein 2 (BMP2), vitamin D, and anti-inflammatory agents; and
   (b) a catabolism inhibitor selected from the group consisting of a bisphosphonate, a cathepsin K inhibitor, a p38 inhibitor, a c-Jun N-terminal kinase (JNK) inhibitor, an IκB kinase (IKK) inhibitor, an NF-κB inhibitor, a calcineurin inhibitor, a nuclear factor of activated T cells (NFAT) inhibitor, and a phosphoinositide 3-kinase (PI3K) inhibitor.

* * * * *